United States Patent [19]

Terashima et al.

[11] Patent Number: 5,231,179
[45] Date of Patent: Jul. 27, 1993

[54] HETEROCYCLIC COMPOUNDS AND THEIR PRODUCTION

[75] Inventors: Shiro Terashima, Tokyo; Yoshio Ito; Takeo Kawabata, both of Sagamihara; Kunikazu Sakai, Tokyo; Tamejiro Hiyama; Yoshikazu Kimura, both of Sagamihara; Makoto Sunagawa, Itami; Katsumi Tamoto, Toyonaka; Akira Sasaki, Ibaraki, all of Japan

[73] Assignee: Sumitomo Pharmaceuticals Company, Limited, Osaka, Japan

[21] Appl. No.: 684,488

[22] Filed: Apr. 12, 1991

Related U.S. Application Data

[63] Continuation of Ser. No. 384,924, Jul. 26, 1989, abandoned, which is a continuation of Ser. No. 6,921, Jan. 27, 1987, abandoned.

[30] Foreign Application Priority Data

Jan. 27, 1986 [JP] Japan ................... 61-13747
Mar. 5, 1986 [JP] Japan ................... 61-46060

[51] Int. Cl.$^5$ ............... C07D 205/00; C07D 263/04; C07D 263/38; C07D 413/06
[52] U.S. Cl. ................... 540/200; 548/229; 548/230
[58] Field of Search ........................... 540/200

[56] References Cited

FOREIGN PATENT DOCUMENTS 0197432 10/1986 European Pat. Off. ............ 548/229
60-42373 3/1985 Japan ........................ 548/230
422743 4/1967 Switzerland .
1482879 8/1977 United Kingdom .

OTHER PUBLICATIONS

Shib et al., "Synthetic Carbapenem Antibiotics...," Heterocycles, vol. 21, No. 1, 1984, pp. 22-44.
Oida et al. "Synthetic Approach Directed at 1-Carbopenams...," Chem. Pharm. Bull., vol. 28, No. 12, 1980, pp. 3494-3500.
Abdel-Magid et al, J. Am. Chem. Soc. 1986, 108, 4595-4602.
Nagao et al, J. Am. Chem. Soc. 1986, 108, 4673-4675.
Evans I: CA 103:37401(c), 1985.
Evans II: CA 108:112900y, 1987.
Evans III: CA 107:237279p, 1987.
Evans IV: CA 108:150929x, 1987.
Aliev, Khim. Getero. Soed. (English language version), v. 3, No. 3, pp. 341-342 (1967).

Primary Examiner—Frederick E. Waddell
Assistant Examiner—Frederick F. Tsung
Attorney, Agent, or Firm—Birch, Stewart, Kolasch & Birch

[57] ABSTRACT

A compound of the formula:

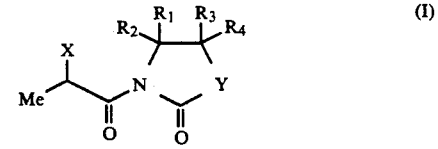

wherein $R_1$, $R_2$, $R_3$ and $R_4$ are each a hydrogen atom, a lower alkyl group, an ar(lower)alkyl group or an aryl group, or $R_1$ and $R_2$ may be combined together to form a lower alkylene group and/or $R_3$ and $R_4$ are combined together to form a lower alkylene group, or $R_1$, $R_2$, $R_3$ and $R_4$ may be combined together to form an o-phenylene group, X is a halogen atom and Y is an oxygen atom or a nitrogen atom substituted with lower alkyl or aryl, which is useful as an intermediate in the synthesis of 1$\beta$-methylcarbapenem compounds valuable as antibiotics.

8 Claims, No Drawings

HETEROCYCLIC COMPOUNDS AND THEIR PRODUCTION

This application is a continuation of application Ser. No. 07/384,924 filed on Jul. 26, 1989, which is continuation of Ser. No. 07/006,921 filed on Jan. 27, 1987, both of which are now abandoned.

The present invention relates to heterocyclic compounds and their production. More particularly, the invention relates to novel heterocyclic compounds useful as intermediates in the synthesis of beta-lactam compounds as well as 1β-methylcarbapenem compounds, and their production.

The heterocyclic compounds of this invention are representable by the formula:

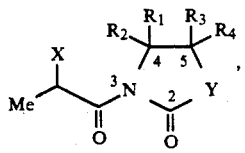

wherein $R_1$, $R_2$, $R_3$ and $R_4$ are each a hydrogen atom, a lower alkyl group, an ar(lower)alkyl group or an aryl group, or $R_1$ and $R_2$ may be combined together to form a lower alkylene group and/or $R_3$ and $R_4$ may be combined together to form a lower alkylene group, or $R_1$, $R_2$, $R_3$ and $R_4$ may be combined together to form an o-phenylene group, X is a halogen atom and Y is an oxygen atom or a nitrogen atom substituted with lower alkyl or aryl.

Beta-Lactam compounds of the formula:

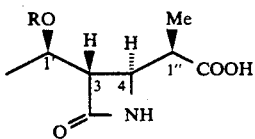

wherein R is a hydrogen atom or a protective group for hydroxyl are known to be useful as intermediates for the synthesis of 1β-methylcarbapenem compounds having a potential antimicrobial activity. They have heretofore been synthesized from the corresponding desmethyl compounds by drawing out the hydrogen atom at the 1″-position in the acetic acid residue at the 4-position by the aid of a strong base and introducing a methyl group therein [Heterocycles, 21, 29 (1984)]. In this method, however, it is essential to use lithium diisopropylamide which can be handled with great difficulty in industry. Further, it is indispensable to perform the reaction at such a low temperature as $-78°$ C. In addition, unnecessary epimers such as beta-lactam derivatives having 1″α-methyl group are by-produced with a relatively large proportion ($1″\beta/1″\alpha = \frac{1}{4}$). It is thus clear that the conventional synthetic method has various drawbacks from an industrial viewpoint.

As a result of an extensive study to overcome the drawbacks present in the conventional synthetic method, it has now been found that the compounds (I) are useful as the starting materials for production of the beta-lactam compounds (IV) and also as the reagents for stereospecific formation of the beta-lactam compounds (IV) at a low cost. This invention is based on the above finding.

Accordingly, it is a main object of this invention to provide the compounds (I) and other intermediates in the synthesis of the beta-lactam compounds (IV). Among the other intermediates, typical ones are representable by the formula:

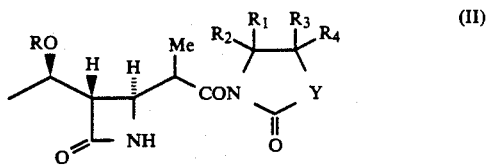

wherein R, $R_1$, $R_2$, $R_3$, $R_4$ and Y are each as defined above.

With respect to the compounds (I) and (II), preferred are those wherein $R_1$, $R_2$, $R_3$ and $R_4$ are each a hydrogen atom, a lower alkyl group or an ar(lower)alkyl group, or $R_1$ and $R_2$ are combined together to form a lower alkylene group and/or $R_3$ and $R_4$ are combined together to form a lower alkylene group. More preferred are those wherein $R_1$ and $R_2$ are each a lower alkyl group, an ar(lower)alkyl group or $R_1$ and $R_2$ are combined together to form a lower alkylene group and $R_3$ and $R_4$ are each a hydrogen atom or a lower alkyl group or $R_3$ and $R_4$ are combined together to form a lower alkylene group and Y is an oxygen atom or a nitrogen atom substituted with lower alkyl.

In this specification, the term "lower" is normally intended to mean a group having not more than 8 carbon atoms, especially not more than 5 carbon atoms. Examples of "lower alkyl" include methyl, ethyl, n-propyl, isopropyl, n-butyl, isobutyl, etc. Examples of "lower alkylene" are ethylene, propylene, trimethylene, tetramethylene, pentamethylene, hexamethylene, etc. The aryl group usually indicates an aromatic carbocyclic group having not more than 20 carbon atoms such as phenyl, naphtyl or anthranyl, which may be optionally substituted with any substituent such as lower alkyl, lower alkoxy, halogen, nitro. Specific examples of the aryl group are phenyl, p-methoxyphenyl, 2,4-dimethoxyphenyl, p-chlorophenyl, etc. The ar(lower)alkyl group may consist of an alkyl group having not more than 5 carbon atoms and at least one aryl group attached thereto, the aryl group being optionally substituted with any substituent such as lower alkyl, lower alkoxy or halogen. Specific examples of the ar(lower)alkyl group are benzyl, p-methoxybenzyl, 2,4-dimethoxybenzyl, p-chlorobenzyl, diphenylmethyl, etc. The term "halogen" covers chlorine, bromine, iodine, etc.

When $R_1$, $R_2$, $R_3$ and $R_4$ are combined together to form an o-phenylene group, the resulting compounds (I) may be represented by the formula:

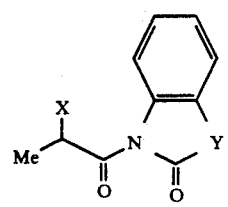

wherein X and Y are each as defined above.

The protective group for hydroxyl may be the one as disclosed in various textbooks such as "Protective Groups in Organic Synthesis" (1981) published by John Wiley & Sons, New York, U.S.A. and "New Experimental Chemistry" ("Shin-Jikken Kagaku Koza" in Japanese), Vol. 14 (1978) published by Maruzen, Tokyo, Japan as well as many literatures cited in those textbooks. Specific examples of the protective group for hydroxyl are a lower alkyl group (e.g. methyl, ethyl, n-propyl, isopropyl, n-butyl, sec-butyl, t-butyl), a substituted methyl group (e.g. methoxymethyl, methylthiomethyl, 2,2,2-trichloroethoxymethyl), a tetrahydropyranyl group, a substituted ethyl group (e.g. 1-ethoxyethyl, 1-methyl-1-methoxyethyl, trichloroethyl), an optionally substituted monophenylmethyl, diphenylmethyl or triphenylmethyl group (e.g. benzyl, p-methoxybenzyl, o-nitrobenzyl, p-nitrobenzyl, p-chlorobenzyl, diphenylmethyl, triphenylmethyl), a substituted silyl group (e.g. trimethylsilyl, triethylsilyl, t-butyldimethylsilyl, t-butyldiphenylsilyl), a formyl group, a lower alkanoyl group (e.g. acetyl, isobutyryl, pivaloyl), a halogenated lower alkanoyl group (e.g. dichloroacetyl, trichloroacetyl, trifluoroacetyl), an arylcarbonyl group (e.g. benzoyl, toluoyl, naphthoyl), a lower alkoxycarbonyl group (e.g. methoxycarbonyl, ethoxycarbonyl, isobutoxycarbonyl), a halogenated lower alkoxycarbonyl group (e.g. 2-iodoethoxycarbonyl, 2,2,2-trichloroethoxycarbonyl), a lower alkenyloxycarbonyl group (e.g. allyloxycarbonyl, 3-methylallyloxycarbonyl), an optionally substituted arylmethyloxycarbonyl group (e.g. benzyloxycarbonyl, p-methoxybenzyloxycarbonyl, 2,4-dimethoxybenzyloxycarbonyl, o-nitrobenzyloxycarbonyl, p-nitrobenzyloxycarbonyl), etc.

The compound (I) can be produced from the compound (V) through the following steps:

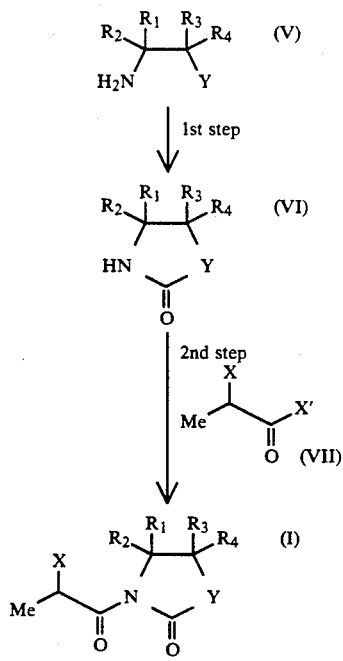

wherein X' is a halogen atom and $R_1$, $R_2$, $R_3$, $R_4$, X and Y are each as defined above.

1st step

The compound (V) is reacted with a carbonic ester (e.g. diethyl carbonate, dimethyl carbonate, benzyl carbonate) in the presence of a base (e.g. lithium carbonate, sodium carbonate, potassium carbonate, sodium hydroxide, potassium hydroxide, sodium methoxide, sodium ethoxide, diisopropylethylamine, triethylamine) to produce the compound (VI). Alternatively, the compound (V) is reacted with phosgene, methyl chlorocarbonate, ethyl chlorocarbonate, benzyl chlorocarbonate or carbonyl diimidazole or its related compound, if necessary, in the presence of a base (e.g. triethylamine, diisopropylethylamine, 1,4-di azabicyclo[2.2.2]octane, 1,8-diazabicyclo[5.4.0]undec-7-ene) to give the compound (VI).

The reaction may be effected in the presence or absence of an inert solvent. Examples of the solvent are alcohols (e.g. methanol, ethanol, propanol, butanol), hydrocarbons (e.g. benzene, toluene, cyclohexane), ethers (e.g. diethyl ether, tetrahydrofuran, dioxane, 1,2-dimethoxyethane), halogenated hydrocarbons (e.g. chloroform, dichloromethane, 1,2-dichloroethane, carbon tetrachloride), etc. The reaction temperature is normally within a range of −20° to 200° C.

2nd step

The compound (VI) is reacted with an alpha-halopropionyl halide (VII) in the presence of a base to give the compound (I).

As the alpha-halopropionyl halide (VII), there may be used alpha-chloropropionyl chloride, alpha-chloropropionyl bromide, alpha-chloropropionyl iodide, alphabromopropionyl chloride, alpha-bromopropionyl bromide, alpha-bromopropionyl iodide, alpha-iodopropionyl chloride, alpha-iodopropionyl bromide, alpha-iodopropionyl iodide, etc. Among them, alpha-bromopropionyl bromide is preferred. Examples of the base are alkali metal hydrides (e.g. lithium hydride, sodium hydride, potassium hydride), alkyl or aryl lithium compounds (e.g. methyl lithium, n-butyl lithium, sec-butyl lithium, t-butyl lithium, phenyl lithium), alkali metals (e.g. sodium, lithium, potassium), etc.

The reaction is normally carried out in an inert solvent. Examples of the inert solvent are ethers (e.g. diethyl ether, tetrahydrofuran, dioxane, 1,2-dimethoxyethane), hydrocarbons (e.g. benzene, toluene, hexane, cyclohexane), halogenated hydrocarbons (e.g. dichloromethane, 1,2-dichloroethane), aprotic polar solvents (e.g. N,N-dimethylformamide, N,N-dimethylacetamide, hexamethylphosphoric triamide), their mixtures, etc. The reaction proceeds usually at a temperature of −80° to 50° C.

After completion of the reaction, the reaction mixture is subjected to an ordinary post-treatment for recovery of the product.

As stated above, the compounds (I) are useful as intermediates in the synthesis of the beta-lactam compounds (IV), which are per se known and can be converted into 1β-methylcarbapenem compounds useful as antibiotics by a conventional procedure. The conversion of the compounds (I) into the beta-lactam compounds (IV) may be accomplished according to the following route:

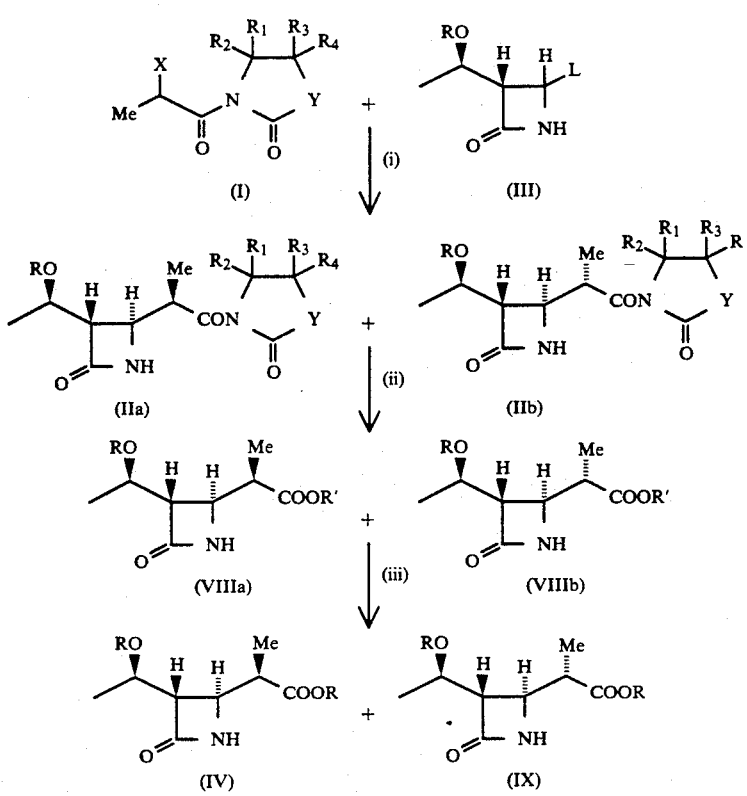

wherein R, $R_1$, $R_2$, $R_3$, $R_4$, X and Y are each as defined above, R' is a lower alkyl group or a substituted or unsubstituted benzyl group and L is a leaving group.

As the leaving group represented by L, a group which is capable of being readily substituted with a nucleophilic reagent is preferred. Examples of the preferred leaving group are an acyloxy group such as substituted or unsubstituted lower alkylcarbonyloxy (e.g. acetoxy, monochloroacetoxy, trichloroacetoxy, trifluoroacetoxy, propionyloxy, butyryloxy) or substituted or unsubstituted arylcarbonyloxy (e.g. benzoyloxy, p-methylbenzoyloxy, p-methoxybenzoyloxy, p-chlorobenzoyloxy, p-nitrobenzoyloxy), a lower alkylsulfonyloxy group (e.g. methanesulfonyloxy, ethanesulfonyloxy, trifluoromethanesulfonyloxy), an arylsulfonyloxy group (e.g. benzenesulfonyloxy, p-toluenesulfonyloxy, p-chlorobenzenesulfonyloxy), a lower alkylsulfonyl group (e.g. methanesulfonyl, ethanesulfonyl), an arylsulfonyl group (e.g. benzenesulfonyl, p-chlorobenzenesulfonyl, p-toluenesulfonyl), an arylthio group (e.g. phenylthio, p-chlorophenylthio), a halogen atom (e.g. chlorine, bromine, iodine). Among them, preferred are substituted or unsubstituted lower alkylcarbonyloxy, substituted or unsubstituted arylcarbonyloxy, etc.

Step (i):

The compound (III) wherein R is a protective group for hydroxyl, which is obtainable by a known process, is reacted with the compound (I) in an inert solvent in the presence of zinc powder to give the compounds (IIa) and (IIb).

The starting compound (III) may be used in the form of each or a mixture of two kinds of diastereomers, of which one is of higher polarity and the other is of lower polarity. Specific examples of the compound (III) are as follows: (1'R,3R,4R)-3-[1'-(t-butyldimethylsilyloxy)ethyl]-4-acetoxyazetidin-2-one, (1'R,3R,4R)-3-[1'-(t-butyldimethylsilyloxy)ethyl]-4-benzoyloxyazetidin-2-one, (1'R, 3R, 4R) -3-[1'-(benzyloxycarbonyloxy)ethyl]-4-acetoxyazetidin-2-one, etc.

As the inert solvent, there may be used any one chosen from ethers (e.g. diethyl ether, dibutyl ether, tetrahydrofuran, dioxane, 1,2-dimethoxyethane), hydrocarbons (e.g. benzene, toluene, hexane, cyclohexane), aprotic polar solvents (e.g. N,N-dimethylformamide, N,N-dimethylacetamide, hexamethylphosphoric triamide), etc. Among them, preferred are tetrahydrofuran, diethyl ether, dioxane, 1,2-dimethoxyethane, N,N-dimethylformamide, etc.

The compound (I) and zinc powder may be used in excessive amounts so as to assure the proceeding of the reaction but, in most cases, are respectively used in amounts of 1 to 3 equivalents and of 2 to 5 equivalents to the compound (III). The reaction may be suppressed or promoted by cooling or heating and is usually carried out at a temperature of $-50°$ to $150°$ C., preferably of $0°$ to $100°$ C. By selection of appropriate reaction conditions, there can be preferentially produced the compound (IIa), which is advantageous for production of the beta-lactam compound (IV).

The compounds (IIa) and (IIb) may be respectively isolated from their mixture as the reaction product by application of a per se conventional separation procedure such as recrystallization or column chromatography. For the reaction in the subsequent step, they may be used alone or in their mixture form.

Step (ii):

The compound (IIa) or (IIb) or their mixture is treated with an alkali metal carbonate (e.g. lithium carbonate, sodium carbonate, potassium carbonate) in a lower alkanol (e.g. methanol, ethanol, n-propanol, n-butanol) or with an alkali metal salt (e.g. lithium salt, sodium salt, potassium salt) of a lower alkanol or a substituted or unsubstituted benzyl alcohol in an inert solvent to give the compounds (VIIIa) or (VIIIb) or their mixture. Examples of the substituent when the benzyl alcohol is substituted are lower alkyl (e.g. methyl, ethyl, n-propyl, isopropyl), lower alkoxy (e.g. methoxy, ethoxy, n-propoxy, isopropoxy), etc. One to three of these substituents may be present on the benzene ring of the benzyl alcohol.

As the inert solvent, there are exemplified ethers (e.g. diethyl ether, tetrahydrofuran, dioxane, 1,2-dimethoxyethane), hydrocarbons (e.g. benzene, toluene, hexane, cyclohexane), aprotic polar solvents (e.g. N,N-dimethylformamide, N,N-dimethylacetamide, hexamethylphosphoric triamide), etc. The reaction proceeds normally at a temperature of −20° to 50° C. within about one hour.

Step (iii):

The compound (VIIIa) or (VIIIb) or their mixture is subjected to treatment for conversion of an ester into a free acid such as hydrolysis or catalytic hydrogenolysis to give the compound (IV) (i.e. the 1″β-methyl-β-lactam compound) or the compound (IX) (i.e. the 1″α-methyl-β-lactam compound) or their mixture.

The treatment may be effected by a per se conventional procedure. When the ester is a benzyl, the following hydrogenolysis is advantageous, because the conversion is accomplished under a mild reaction condition. Namely, the compound (VIIIa) or (VIIIb) or their mixture is treated with hydrogen in an inert solvent in the presence of a catalyst such as palladium, platinum or rhodium deposited on carbon at a temperature of −20° to 100° C. under atmospheric pressure. Examples of the inert solvent are ethers (e.g. diethyl ether, tetrahydrofuran, dioxane, 1,2-dimethoxyethane), and hydrocarbons (e.g. benzene, toluene, hexane, cyclohexane), etc.

Recovery of the desired compound (IV) from the reaction mixture may be achieved by a per se conventional separation procedure such as recrystallization or column chromatography.

Among the compounds (IIa) obtained in the step (i), the compound of the formula:

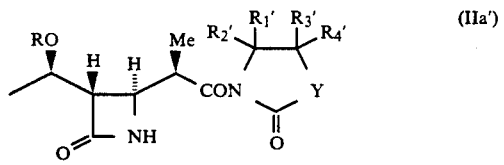

wherein R and Y are each as defined above, $R_1'$ and $R_2'$ are the same and are each a lower alkyl group, an ar(-lower)alkyl group or an aryl group or combined together to form a lower alkylene group and $R_3'$ $R_4'$ are each a hydrogen atom, a lower alkyl group, an ar(lower)alkyl group or an aryl group or combined together to form a lower alkylene group, can be obtained with high stereospecific selectivity by selection of appropriate reaction conditions without using the compound (I) which has a chiral carbon atom at the 4-position on ring structure. Further, the compound (IIa′) is highly crystallizable so that its recovery with a high purity can be readily accomplished by recrystallization. In addition, it can be easily converted into the compound (IV) by solvolysis. Due to these reasons, the compound (IIa′) may be said to be particularly advantageous from an industrial viewpoint.

The present invention will now be illustrated in greater detail with reference to the following Examples and Reference Examples, but it should be understood that these examples are given only for illustrative purposes and are not limitative of the present invention.

In examples and reference examples, the following abbreviations are used:

Ac: acetyl group
TBDMS: t-butyldimethylsilyl group
Me: methyl group
Et: ethyl group
Ph: phenyl group
Z: benzyloxycarbonyl group

EXAMPLE 1-(1)

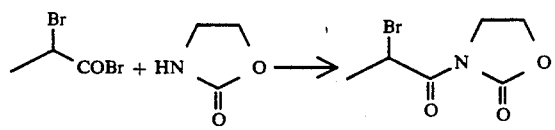

To a solution of oxazolidin-2-one (4.00 g; 45.9 mmol) in dry tetrahydrofuran (70 ml), a solution of n-butyl lithium in hexane (1.60 N; 30 ml) was added at 0° C., and then 1-bromopropionyl bromide (5.83 ml, 45.9 mmol) was added at the same temperature. After 1 hour, an aqueous solution of saturated potassium dihydrogen phosphate (5 ml) was added to decompose the excess reaction agent. The aqueous layer was extracted with ethyl acetate, and the combined organic layer was washed with brine and dried over anhydrous magnesium sulfate. After distilling off the solvent, the residue was purified by silica gel column chromatography (n-hexane:dichloromethane = 1:1) to give 3-(2′-bromopropionyl)oxazolidin-2-one (8.68 g, yield, 84%) as a colorless solid. The sample for analysis was obtained by recrystallization from diethyl ether. M.P., 41° C.

IR (KBr): 1779, 1707, 1400, 1372, 1269, 1240, 1230, 1070, 758 cm$^{-1}$;

H-NMR δ(CDCl$_3$) 1.83 (3H, d, J=6.8 Hz), 4.08 (2H, m), 4.48 (2H, m), 5.69 (1H, q, J=6.8 Hz);

Mass m/e: 223, 221 (M+), 142 (M-80)+;

Elementary analysis for C$_6$H$_8$NO$_3$Br:

Calcd.: C, 32.46; H, 3.63; N, 6.31%.
Found: C, 32.50; H, 3.59; N, 6.29%.

EXAMPLE 1-(2)

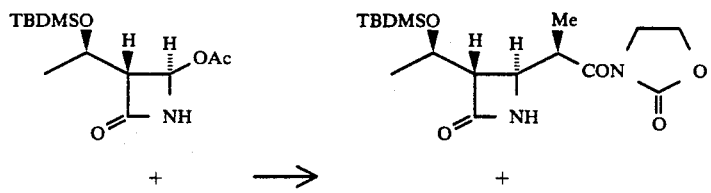

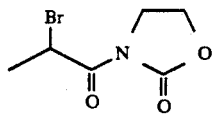

-continued

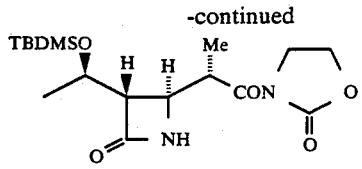

A mixture of 3-(2'-bromopropionyl)oxazolidin-2-one (0.318 g; 1.43 mmol) and (1'R,3R,4R)-3-[1'-(t-butyldimethylsilyloxy)ethyl]-4-acetoxyazetidin-2-one ([α]$^{20}_D$+47.4°, c=1.14, CHCl$_3$) (0.205 g; 0.71 mmol) and zinc powder (0.14 g) in tetrahydrofuran (7 ml) was vigorously stirred at room temperature for 10 minutes. To the reaction mixture, a phosphate buffer (4.0 ml) was added to decompose the excess reaction agent. After extraction with dichloromethane (40 ml), the organic layer was dried over anhydrous magnesium sulfate, and the solvent was distilled off under reduced pressure. The resulting solid residue was purified by silica gel column chromatography (hexane:dichloromethane=1:1~dichloromethane:acetone=9:1). From the less polar fraction, there was obtained (1'R,1''R,3S,4R)-3-[1'-(t-butyldimethylsilyloxy)ethyl]-4-[1''-(oxazolidin-2'''-one-3'''-carbonyl)ethyl]azetidin-2-one (0.116 g, yield, 44%) as a colorless caramel. The sample for analysis was obtained by recrystallization from a mixed solvent of cyclohexane and ethyl acetate (9:1). M.P., 66°-67° C.

[α]$^{27}_D$−6.7° (c=0.63, CHCl$_3$);

IR (KBr): 2950, 1760, 1700, 1390, 1250, 1100, 833, 780 cm$^{-1}$;

H-NMR δ(CDCl$_3$) 0.07 (6H, s), 0.87 (9H, s), 1.21 (3H, d, J=6 Hz), 1.22 (3H, d, J=8 Hz), 3.02 (1H, m), 5.95 (1H, bs);

Mass m/e: 355 (M-15)$^+$, 327 (M-43)$^+$, 313 (M-57)$^+$.

Elementary analysis for C$_{17}$H$_{30}$N$_2$O$_5$Si:

Calcd.: C, 55.11; H, 8.16; N, 7.56%.

Found: C, 55.06; H, 8.25; N, 7.20%.

From the more polar fraction, there was obtained (1'R,1''S,3S,4R)-3-[1'-(t-butyldimethylsilyloxy)ethyl]-4-[1''-(oxazolidin-2'''-one-3'''-carbonyl)ethyl]azetidin-2-one (0.142 g, yield, 53%) as a colorless solid. A sample for analysis was obtained by recrystallization from a mixed solvent of cyclohexane and ethyl acetate (7:3). M.P., 177°-180° C.

[α]$^{28}_D$+31.4° (c=0.94, CHCl$_3$);

IR (KBr): 2950, 1780, 1762, 1694, 1390, 1218, 1107, 1047, 830 cm$^{-1}$;

H-NMR δ(CDCl$_3$) 0.08 (6H, s), 0.89 (9H, s), 1.25 (3H, d, J=6.2 Hz), 1.28 (3H, d, J=6.6 Hz), 2.83 (1H, m), 5.98 (1H, bs);

Mass m/e: 355 (M-15)$^+$, 327 (M-43)$^+$, 313 (M-57)$^+$.

Elementary analysis for C$_{17}$H$_{30}$N$_2$O$_5$Si:

Calcd.: C, 55.11; H, 8.16; N, 7.56%.

Found: C, 54.84; H, 8.24; N, 7.40%.

REFERENCE EXAMPLE 1

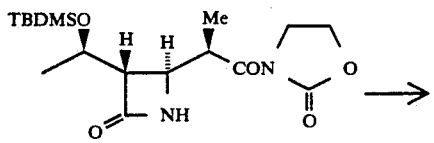

-continued

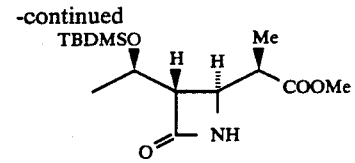

(1'R,1''R,3S,4R)-3-[1'-(t-Butyldimethylsilyloxy)ethyl]-4-[1''-(oxazolidin-2'''-one-3'''-carbonyl)ethyl]-azetidin-2-one prepared in Example 1-(2) (6.3 mg; 0.017 mmol) was dissolved in dry methanol (0.5 ml), to which anhydrous potassium carbonate (10 mg, 0.073 mmol) was added, and the mixture was vigorously stirred at room temperature for 30 minutes. To the resulting mixture, ether and a saturated aqueous solution of potassium dihydrogen phosphate were added to stop the reaction, and the aqueous layer was extracted with ether. The combined organic layers were dried over anhydrous sodium sulfate, and the solvent was distilled off under reduced pressure to give a colorless solid, which was purified by silica gel column chromatography to give (1'R,1''R,3S,4S)-3-[1'-(t-butyldimethoxy)ethyl]-4-[1''-(methoxycarbonyl)ethyl]azetidin-2-one (1.9 mg, yield, 35%) as a colorless solid. M.P., 121°-122° C.

[α]$^{20}_D$−24.4° (c=0.25, CH$_2$Cl$_2$);

IR (KBr): 2950, 2850, 1761, 1737, 1470, 1370, 1341, 1250, 1198, 1162, 958, 830, 772 cm$^{-1}$;

H-NMR δ(CDCl$_3$) 0.07 (6H, s), 0.87 (9H, s), 1.17 (3H, d, J=6.2 Hz), 1.23 (3H, d, J=6.0 Hz), 2.71 (1H, m), 2.99 (1H, m), 3.70 (3H, s), 3.87 (1H, dd, J=2.5 and 5 Hz), 4.21 (1H, m), 5.87 (1H, bs);

Mass m/e: 300 (M-15)$^+$, 258 (M-57)$^+$.

Elementary analysis for C$_{15}$H$_{29}$NO$_4$Si:

Calcd.: C, 57.11; H, 9.26; N, 4.44%.

Found: C, 57.14; H, 9.12; N, 4.33%.

EXAMPLE 2-(1)

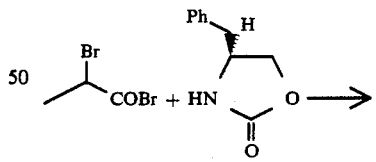

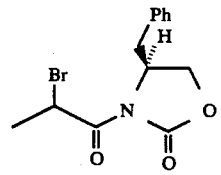

To a solution of (4S)-4-benzyloxazolidin-2-one (0.164 g; 0.927 mmol) in dry tetrahydrofuran (3.8 ml), a 1.62 N solution of n-butyl lithium in hexane (0.571 ml; 0.927 mmol) was added at 0° C., and then 2-bromopropionyl bromide (0.106 ml; 1.01 mmol) was added at the same temperature. After 10 minutes, an aqueous solution of saturated sodium hydrogen carbonate (1 ml) was added to decompose the excess reaction agent. The reaction mixture was diluted with ethyl acetate, washed with brine and dried over anhydrous magnesium sulfate. After distilling off the solvent, the resulting solid was purified by silica gel chromatography (hexane:dichloromethane=2:3–0:1) to give a less polar (4S)-3-(2'-bromopropionyl)-4-benzyloxazolidin-2-one (0.137 g, yield, 47%) and a (4S)-3-(2'-bromopropionyl)-4-benzyloxazolidin-2-one (0.145 g, yield, 50%).

Analysis Data

Less polar (4S)-3-(2'-bromopropionyl)-4-benzyloxazolidin-2-one, oily product:

$[\alpha]^{23}_D +68.4°$ (c=1.33, AcOEt);

IR (neat): 1786, 1709, 1394, 1373, 1251, 1200, 740, 700 cm$^{-1}$;

H-NMR δ(CDCl$_3$) 1.88 (3H, d, J=6.6 Hz), 2.79 (1H, dd, J=9.7 and 13.4 Hz), 3.32 (1H, dd, J=3.3 and 13.4 Hz), 4.23 (1H, d, J=3.7 Hz), 3.24 (1H, d, J=6.6 Hz), 4.16 (1H, m), 5.72 (1H, q, J=6.6 Hz), 7.29 (5H, m);

Mass m/e: 313, 311 (M+);

Elementary analysis for C$_{13}$H$_{14}$NO$_3$Br:
Calcd.: C, 50.02; H, 4.52; N, 4.49%.
Found: C, 49.97; H, 4.67; N, 4.47%.

More polar (4S)-3-(2'-bromopropionyl)-4-benzyloxazolidin-2-one, colorless crystals, M.P., 142°–144

$[\alpha]^{23}_D +92.5°$ (c=1.25, AcOEt);

IR (KBr): 1781, 1706, 1380, 1300, 1248, 1210, 1201, 1180, 1120, 1101, 1016, 991, 952, 760, 740, 701 cm$^{-1}$;

H-NMR δ(CDCl$_3$) 1.87 (3H, d, J=6.8 Hz), 2.79 (1H, dd, J=9.4 and 13.4 Hz), 3.33 (1H, dd, J=3.3 and 13.4 Hz, 4.22 (2H, d, J=5.3 Hz), 4.70 (1H, m), 5.73 (1H, q, J=6.8 Hz), 7.30 (5H, m);

Mass m/e: 313, 311 (M+);

Elementary analysis for C$_{13}$H$_{14}$NO$_3$Br):
Calcd.: C, 50.02; H, 4.52; N, 4.49%.
Found: C, 49.97; H, 4.67; N, 4.47%.

EXAMPLE 2-(2)

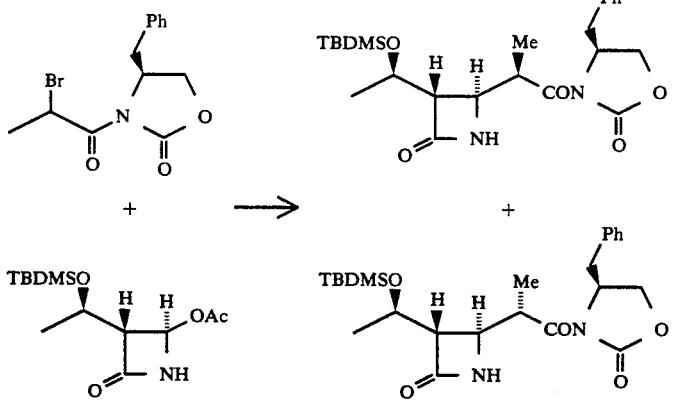

More polar (4S)-3-(2'-bromopropionyl)-4-benzyloxazolidin-2-one (68.3 mg; 0.219 mmol) and (1'R,3R,4R)-3-[1'-(t-butyldimethylsilyloxy)ethyl]-4-acetoxyazetidin-2-one (31.4 mg; 0.109 mmol) were dissolved in dry tetrahydrofuran (1.1 ml), to which zinc powder (25 mg) was added at 0° C., and the mixture was vigorously stirred for 30 minutes at the same temperature. By the same treatment as in Example 1-(2), there was obtained (1'R,1''R,3S,4R,4'''S)-3-[1'-(t butyldimethylsilyoxy)ethyl]2'''-one-3'''-carbonyl)ethyl]azetidin-2-one (41.3 mg, yield, 82%) as colorless crystals. The sample for analysis was obtained by recrystallization from a mixed solvent of n-hexane and ethyl acetate. M.P., 115°–116° C.

$[\alpha]^{20}_D +25°$ (c=0.74, CHCl$_3$);

H-NMR δ(CDCl$_3$) 0.09 (6H, s), 0.90 (9H, s), 1.23 (3H, d, 6.8 Hz), 1.25 (3H, d, J=6.2 Hz), 2.69 (1H, dd, J=10.1 and 13.4 Hz), 3.08 (1H, m), 3.33 (1H, dd, J=3.4 and 13.4 Hz), 3.96 (1H, m), 4.70 (1H, m), 5.94 (1H, bs), 7.29 (5H, m);

Mass m/e: 403 (M-57)+;

Elementary analysis for C$_{24}$H$_{36}$N$_2$O$_5$Si):
Calcd.: C, 62.58; H, 7.88; N, 6.08%.
Found: C, 62.53; H, 8.05; N, 6.01%.

Also, there was obtained from the more polar fraction (1'R,1''S,3S,4R,4'''S)-3-[1'-(t-butyldimethylsilyloxy)ethyl]-4-[1''-(4'''-benzyloxazolidin-2'''-one-3'''-carbonyl)ethyl]azetidin-2-one (4.6 mg, yield, 9.1%). The sample for analysis was obtained by recrystallization from a mixed solvent of n-hexane and ethyl acetate. Colorless crystals. M.P., 143°–144° C.

$[\alpha]^{20}_D +78°$ (c=0.18, CHCl$_3$);

IR (KBr): 2950, 1780, 1763, 1700, 1390, 1254, 1236, 1190, 1106, 838, 778 cm$^{-1}$;

H-NMR δ(CDCl$_3$) 0.10 (6H, s), 0.90 (9H, s), 1.27 (3H, d, 6.3 Hz), 1.32 (3H, d, J=6.6 Hz), 2.79 (1H, dd, J=9.4 and 13.4 Hz), 2.81 (1H, m), 3.25 (1H, dd, J=3.5 and 13.4 Hz), 4.73 (1H, m), 5.84 (1H, bs), 7.28 (5H, m);

Mass m/e: 403 (M-57)+;

Elementary analysis for C$_{24}$H$_{36}$N$_2$O$_5$Si):
Calcd.: C, 62.58; H, 7.88; N, 6.08%.
Found: C, 62.60; H, 7.78; N, 6.03%.

REFERENCE EXAMPLE 2-(1)

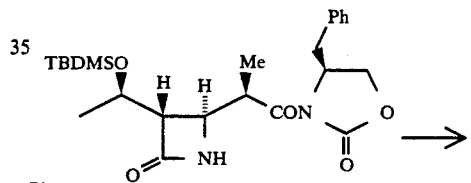

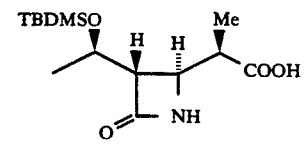

(1'R,1''R,3S,4R,4'''S)-3-[1'-(t-Butyldimethylsilyloxy)ethyl]-4-[1''-(4'''-benzyloxazolidin-2'''-one-3'''-carbonyl)ethyl]azetidin-2-one (30.0 mg; 0.065 mmol) was treated in the same manner as in Reference Example 3-(1) to give (1'R,1"R,3S,4S)-3-[1'-(t-butyldimethylsilyloxy) ethyl]-4-(1"-carboxyethyl)azetidin-2-one (7.5 mg, yield, 38%).

The product was identical to that obtained in Reference Example 3-(1) with respect to melting point, optical rotation, IR, H-NMR and Mass spectra.

REFERENCE EXAMPLE 2-(2)

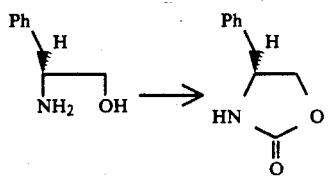

To a mixture of (2S)-2-amino-3-phenyl-1-propanol (0.649 g; 4.29 mmol) and diethyl carbonate (1.04 ml; 8.58 mmol), anhydrous potassium carbonate (20 mg; 0.14 mmol) was added, and the mixture was stirred at 120° to 130° C. for 3 hours. After cooling, to the resulting mixture 1N hydrochloric acid (1.5 ml) and ethyl acetate (about 50 ml) were added and stirred. The organic layer was separated and washed with brine, and dried over anhydrous magnesium sulfate. Distilling off the solvent under reduced pressure gave (4S)-4-benzyloxazolidin-2-one (0.760 g, quantitative yield) as a colorless solid. The sample for analysis was obtained by recrystallization from a mixed solvent of cyclohexane and toluene (1:1). Colorless crystals. M.P., 88°–89° C.

$[\alpha]^{23}_D$ −57.5° (c=1.58, CHCl₃);

IR (KBr): 1751, 1711, 1408, 1246, 1020, 944, 760, 710, 619, 530 cm⁻¹;

H-NMR δ(CDCl₃): 2.87 (2H, d, J=6.2 Hz), 5.11 (1H, bs), 7.29 (5H, m);

Mass m/e: 177 (M⁺);

Elementary analysis for C₁₀H₁₁NO₂:
Calcd.: C, 67.78; H, 6.26; N, 7.90%.
Found: C, 67.82; H, 6.34; N, 7.86%.

EXAMPLE 3-(1)

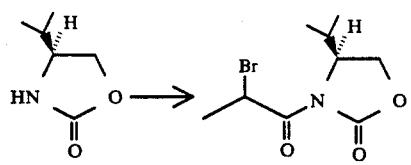

(4S)-4-Isopropyloxazolidin-2-one (0.156 g; 1.21 mmol) was treated in the same manner as in Example 2-(1) to obtain a less polar (4S)-3-(2'-bromopropionyl)-4-isopropyloxazolidin-2-one (0.177 g, yield, 55%) a more polar (4S)-3-(2'-bromopropionyl)-4-isopropyloxazolidin-2-one (0.134 g, yield, 42%).

Analysis Data

Less polar (4S)-3-(2'-bromopropionyl)-4-isopropyloxazolidin-2-one, colorless crystals (from n-hexane-ether), M.P., 41°–42.5° C.:

$[\alpha]^{23}_D$ +70.0° (c=1.30, AcOEt);

IR (KBr): 2980, 1785, 1698, 1390, 1370, 1300, 1259, 1201, 1090, 1058, 700 cm⁻¹;

H-NMR δ(CDCl₃) 0.89 (3H, d, J=7.0 Hz), 0.94 (3H, d, J=7.0 Hz), 1.85 (3H, d, J=6.8 Hz), 2.38 (1H, m), 5.57 (1H, q, J=6.8 Hz);

Mass m/e: 265, 263 (M⁺);

Elementary analysis for C₉H₁₄BrNO₃:
Calcd.: C, 40.93; H, 5.34; N, 5.30%.
Found: C, 40.80; H, 5.34; N, 5.22%.

More polar (4S)-3-(2'-bromopropionyl)-4-isopropyloxazolidin-2-one, colorless crystals, M.P., 56° C.:

$[\alpha]^{23}_D$ +92.0° (c=1.04, AcOEt);

IR (KBr): 2970, 1784, 1768, 1710, 1400, 1370, 1250, 1210, 1120, 1062 cm⁻¹;

H-NMR δ(CDCl₃) 0.94 (3H×2, d, J=7 Hz), 1.82 (3H, d, J=6.8 Hz), 2.40 (1H, m), 5.76 (1H, q, J=6.8 Hz);

Mass m/e: 265, 263 (M⁺);

Elementary analysis for C₉H₁₄BrNO₃:
Calcd.: C, 40.93; H, 5.34; N, 5.30%.
Found: C, 40.75; H, 5.48; N, 5.26%.

EXAMPLE 3-(2)-1

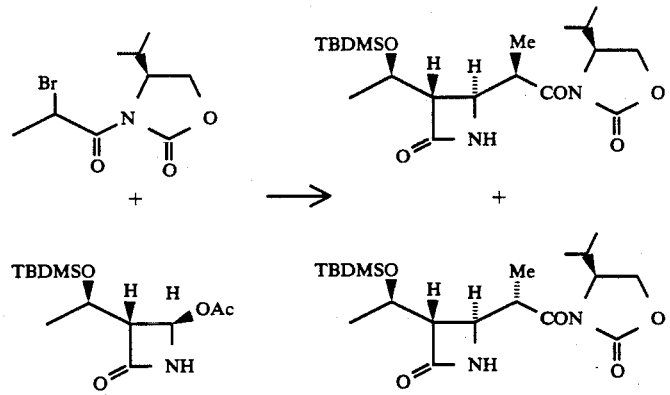

Less polar (4S)-3-(2'-bromopropionyl)-4-isopropyloxazolidin-2-one (26.2 mg; 0.099 mmol) and (1'R,3R,4R)-3-[1'-(t-butyldimethylsilyloxy)ethyl]-4-acetoxyazetidin-2-one (14.0 mg; 0.049 mmol) were dissolved in dry tetrahydrofuran (0.5 ml), to which zinc powder (13 mg) was added at 25° C., and the mixture was vigorously stirred for 10 minutes. By adding a phosphate buffer (pH 7) (0.3 ml) and dichloromethane (5 ml), the reaction was stopped, and the organic layer was separated and dried over anhydrous magnesium sulfate, and the solvent was distilled off under reduced pressure. The resulting residue was purified by silica gel column chromatography (dichloromethane:ethyl acetate=1:0–4:1). From the less polar fraction there was obtained (1'R,1"R,3S,4R,4'"S)-3-[1'-(t-butyldimethylsilyloxy)ethyl]4-[1"-(4'"-isopropyloxazolidin-2'"-one-3'"-carbonyl)ethyl]-azetidin-2-one (17.4 mg, yield, 88%) as colorless crystals. M.P., 123°–124° C.

[α]$^{23}_{D}$+27.1° (c=1.15, CHCl$_3$);

IR (KBr): 1780, 1699, 1390, 1206, 834, 777 cm$^{-1}$;

H-NMR δ(CDCl$_3$) 0.07 (6H, s), 0.87 (9H, s), 0.88 (3H, d, J=6.8 Hz), 0.93 (3H, d, J=6 Hz), 1.19 (3H, d, J =6.8 Hz), 1.23 (3H, d, J=6.2 Hz), 2.34 (1H, m), 3.93 (1H, m), 5.99 (1H, bs);

Mass m/e: 355 (M-57)$^+$;

Elementary analysis for C$_{20}$H$_{36}$N$_2$O$_5$Si:

Calcd.: C, 58.22; H, 8.79; N, 6.79%.

Found: C, 58.07; H, 9.07; N, 6.78%.

Further, from the more polar fraction, there was obtained (1'R,1"S,3S,4R,4'"S)-3-[1'-(t-butyldimethylsilyloxy)ethyl]-4-[1'"-isopropyloxazolidin-2'"-one-3'"-carbonyl)ethyl]azetidin-2-one (2.4 mg, yield, 12%) as colorless crystals. M.P., 176°–177° C.

[α]$^{22}_{D}$+80.8° (c=0.30, CHCl$_3$);

IR (KBr): 1781, 1765, 1700, 1390, 1261, 1103, 803 cm$^{-1}$;

H-NMR δ(CDCl$_3$) 0.08 (6H, s), 0.88 (9H, s), 0.88 (3H, d, J=6.6 Hz), 1.25 (3H, d, J=6.2 Hz), 1.32 (3H, d, J=5.9 Hz), 2.32 (1H, m), 2.80 (1H, dd, J=1.3 and 5.3 Hz), 5.80 (1H, bs);

Mass m/e: 355 (M-57)$^+$;

Elementary analysis for C$_{20}$H$_{36}$N$_2$O$_5$Si:

Calcd.: C, 58.22; H, 8.79; N, 6.79%.

Found: C, 58.17; H, 8.97; N, 6.64%.

EXAMPLE 3-(2)-2

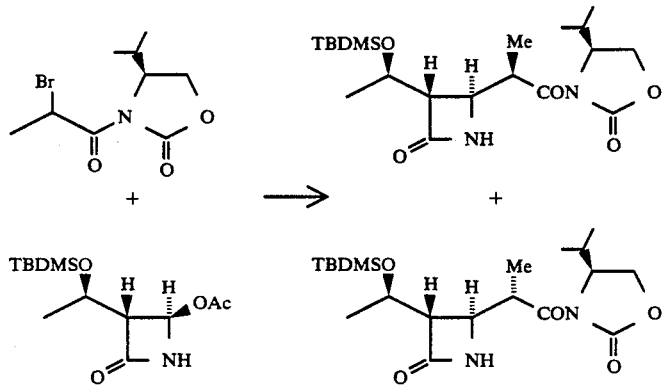

More polar (4S)-3-(2'-bromopropionyl)-4-isopropyloxazolidin-2-one (26.5 mg; 0.100 mmol) and (1'R,3R,4R)-3-[1'-(t-butyldimethylsilyloxy)ethyl]-4-acetoxyazetidin-2-one (14.3 mg; 0.050 mmol) were dissolved in dry tetrahydrofuran (0.5 ml), to which zinc powder (13 mg) was added at 25° C., and the mixture was vigorously stirred for 10 minutes. In the same manner as in Example 3-(2)-1, there were obtained (1'R,1"R,3S,4R,4'"S)-3-[1'-(t-butyldimethylsilyloxy)ethyl] -4'"-isopropyloxazolidin-2'"-one-3'"-carbonyl)ethyl]-azetidin-2-one (17.6 mg, yield, 88%) and (1'R,1"S,3S,4R,4'"S)-3-[1'-(t-butyldimethylsilyloxy)ethyl]-4-[1"-(4'"-isopropyloxazolidin-2'"-one-3'"-carbonyl)ethyl]-azetidin-2-one (2.4 mg, yield, 12%).

The resulting products were identical to those obtained in Example 3-(2)-1 in with respect to melting point, optical rotation, IR, H-NMR and Mass spectra.

EXAMPLE 3-(2)-3

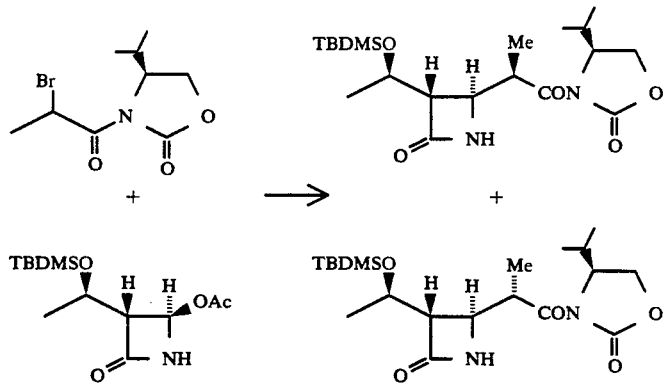

A mixture of less polar and more polar (4S)-3-(2'-bromopropionyl)-4-isopropyloxazolidin-2-one (mixing ratio=1) (26.3 mg; 0.099 mmol) and (1'R,3R,4R)-3-[1'-(t-butyldimethylsilyloxy)ethyl]-4-acetoxyazetidin-2-one (14.1 mg; 0.049 mmol) were dissolved in dry tetrahydrofuran (0.5 ml), to which zinc powder (13 mg) was added at 25° C., and the mixture was vigorously stirred for 10 minutes. In the same manner as in Example 3-(2)-1, there were obtained (1'R,1''R,3S,4R,4'''S)-3-[1'-(t-butyldimethylsilyloxy)ethyl] -4'''-isopropyloxazolidin-2'''-one-3'''-carbonyl)ethyl]-azetidin-2-one (17.5 mg, yield, 87%) and (1'R,1''S,3S,4R,4'''S)-3-[1'-(t-butyldimethylsilyloxy)ethyl]-4-[1''-(4'''-isopropyloxazolidin-2'''-one-3'''-carbonyl)ethyl]-azetidin-2-one (2.3 mg, yield, 11%).

The resulting products were identical to those obtained in Example 3-(2)-1 in with respect to melting point, optical rotation, IR, H-NMR and Mass spectra.

REFERENCE EXAMPLE 3-(1)

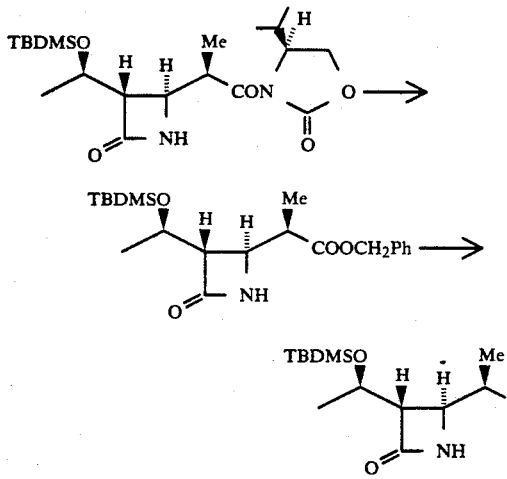

(1'R,1''R,3S,4R,4'''S)-3-[1'-(t-Butyldimethylsilyloxy)ethyl]-4-[1''-(4'''-isopropyloxazolidin-2'''-one-3'''-carbonyl)ethyl]azetidin-2-one (41.2 mg, 0.100 mmol) was dissolved in dry tetrahydrofuran (0.5 ml), to which a 0.5 M solution of lithium benzyl alkoxide in tetrahydrofuran (0.4 ml) was added at 0° C. After stirring the mixture at the same temperature for 1 hour, an aqueous solution of saturated potassium dihydrogen phosphate (0.4 ml) was added to stop the reaction. The reaction mixture was extracted with dichloromethane, and the extract was dried over anhydrous magnesium sulfate to distill off the solvent under reduced pressure. The residue was dissolved in ethyl acetate (1 ml), to which 10% palladium carbon (4 mg) was added, and the mixture was stirred under a hydrogen atmosphere (normal pressure) at room temperature for 4 hours. The catalyst was removed by filtration through a celite column, and the solvent was distilled off under reduced pressure. The resulting solid was purified by silica gel column chromatography (dichloromethane:ethyl acetate:acetic acid=3:1:0.02) to give (1'R,1''R,3S,4S)-3-[1'-(t-butyldimethylsilyloxy)ethyl]-4-(1''-carboxyethyl)azetidin-2-one (20.2 mg, yield, 67%). The sample for analysis was obtained by recrystallization from a mixed solvent of cyclohexane and ethyl acetate. Colorless crystals, M.P., 147°-148° C. (decomp.).

$[\alpha]^{25}_D$ −32.4° (c=0.17, CH$_3$OH);
IR (KBr): 3280, 2950, 1720, 1460, 1280, 1259, 1142, 1040, 839, 780 cm$^{-1}$;
H-NMR δ(CDCl$_3$) 0.07 (6H, s), 0.87 (9H, s), 1.19 (3H, d, J=5.7 Hz), 1.26 (3H, d, J=6.6 Hz), 2.74 (1H, m), 3.03 (1H, m), 3.94 (1H, m), 4.20 (1H, m), 6.25 (1H, bs);
Mass m/e: 286 (M-15)$^+$, 244 (M-57)$^+$;
Elementary analysis for C$_{14}$H$_{27}$NO$_4$Si:
Calcd.: C, 55.78; H, 9.03; N, 4.65%.
Found: C, 55.63; H, 9.19; N, 4.49%.

REFERENCE EXAMPLE 3-(2)

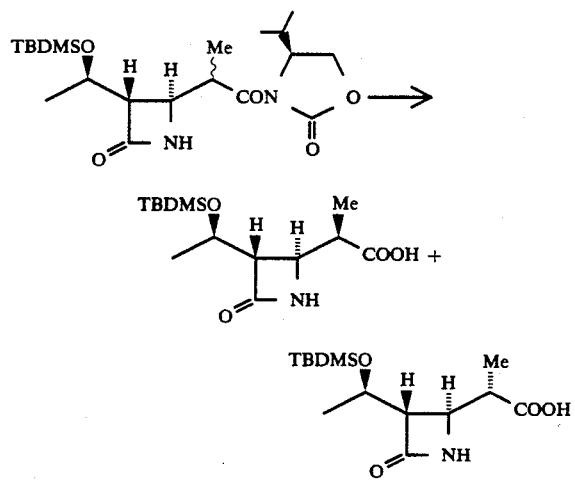

A mixture of (1'R,1''R,3S,4R,4'''S)- and (1'R,1''S,3S,4R,4'''S)-3-[1'-(t-butyldimethylsilyloxy)ethyl]-4-[1''-(4'''-isopropyloxazolidin-2'''-one-3'''-carbonyl)ethyl]-azetidin-2-one (mixing ratio, 88:12) (45.3 mg; 0.110 mmol) was treated in the same manner as in Reference Example 3-(1) to obtain (1'R,1''R,3S,4S)-3-[1'-(t-butyldimethylsilyloxy)-ethyl]-4-(1''-carboxyethyl)azetidin-2-one (19.0 mg, yield, 58% and (1'R,1''S,3S,4S)-3-[1'-(t-butyldimethylsilyloxy) -ethyl-4-(1''-carboxyethyl)azetidin-2-one (2.6 mg, yield, 7.5%).

(1'R,1''R,3S,4S)-form was identical to that obtained in Reference Example 3-(1) in with respect to melting point, optical rotation, IR, H-NMR and Mass spectra.

Analysis data of (1'R,1''S,3S,4S)-form, colorless crystals, M.P., 176°-180° C. (decomp.), are as follows:
$[\alpha]^{20}_D$ −5.0° (c=0.44, CH$_3$OH);
IR (KBr): 3310, 2950, 1720, 1380, 1257, 1048, 962, 840, 776 cm$^{-1}$;
H-NMR δ(CDCl$_3$) 0.08 (6H, s), 0.88 (9H, s), 1.25 (3H, d, J=6.4 Hz), 1.28 (3H, d, J=7.0 Hz), 2.65 (1H, m), 2.81 (1H, m), 3.70 (1H, dd, J=1.9 and 9.8 Hz), 4.19 (1H, m), 6.49 (1H, bs);
Mass m/e: 286 (M-15)$^+$, 244 (M-57)$^+$;
Elementary analysis for C$_{14}$H$_{27}$NO$_4$Si:
Calcd.: C, 55.78; H, 9.03; N, 4.65%.
Found: C, 55.87; H, 9.16; N, 4.56%.

REFERENCE EXAMPLE 3-(3)

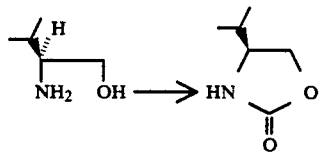

(2S)-2-Amino-3-methyl-1-butanol (0.768 g; 7.44 mmol) was treated in the same manner as in Reference Example 2-(2) to obtain (4S)-4-isopropyloxazolidin-2-one (0.888 g, yield, 92%). The sample for analysis was obtained by recrystallization from a mixed solvent of cyclohexane and toluene (1:1). Colorless crystals, M.P., 72°-73° C.

$[\alpha]^{23}_D +7.46°$ (c=1.37, CHCl$_3$);
IR (KBr): 1752, 1730, 1409, 1248, 1092, 1010, 939, 770 cm$^{-1}$;
H-NMR δ(CDCl$_3$) 0.90 (3H, d, J=6.6 Hz), 0.96 (3H, d, J=6.6 Hz), 1.70 (1H, m), 3.60 (1H, m), 4.10 (1H, dd, J=6.3 and 8.7 Hz), 4.45 (1H, t, J=8.7 Hz), 6.10 (1H, bs);
Mass m/e: 129 (M$^+$);
Elementary analysis for C$_6$H$_{11}$NO$_2$:
Calcd.: C, 55.80; H, 8.58; N, 10.84%.
Found: C, 55.85; H, 8.47; N, 10.78%.

EXAMPLE 4-(1)

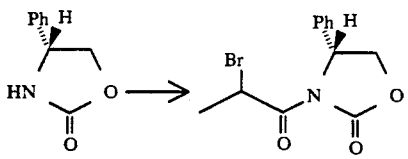

(4R)-4-Phenyloxazolidin-2-one (0.277 g; 1.70 mmol) was treated in the same manner as in Example 2-(1) to obtain a less polar (4R)-3-(2'-bromopropionyl)-4-phenyloxazolidin -2-one (0.295 g, yield, 59%) and a more polar (4R)-3-(2'-bromopropionyl)-4-phenyloxazolidin-2-one (0.196 g, yield, 39%).

Analysis Data

Less polar (4R)-3-(2'-bromopropionyl)-4-phenyloxazolidin-2-one, colorless crystals, M.P., 136°-137° C.:
$[\alpha]^{23}_D -122°$ (c=1.31, AcOEt);
IR (KBr): 1782, 1700, 1380, 1302, 1198, 1180, 1121, 1039, 701 cm$^{-1}$;
H-NMR δ(CDCl$_3$): 1.76 (3H, d, J=6.8 Hz), 4.33 (1H, dd, J=3.1 and 8.8 Hz), 4.75 (1H, dd, J=8.4 and 8.8 Hz), 5.42 (1H, dd, J=3.1 and 8.4 Hz), 5.72 (1H, q, J=6.8 Hz), 7.35 (5H, m);
Mass m/e: 299, 297 (M$^+$);
Elementary analysis for C$_{12}$H$_{12}$BrNO$_3$:
Calcd.: C, 48.34; H, 4.06; N, 4.70%.
Found: C, 48.31; H, 3.96; N, 4.61%.
More polar (4R)-3-(2'-bromopropionyl)-4-phenyloxazolidin-2-one, colorless crystals, M.P., 151°-154° C.:
$[\alpha]^{23}_D -81.6°$ (c=1.06, AcOEt);
IR (KBr): 1784, 1709, 1364, 1330, 1256, 1203, 1060, 757, 696 cm$^{-1}$;
H-NMR δ(CDCl$_3$) 1.77 (3H, d, J=6.8 Hz), 4.27 (1H, dd, J=5.1 and 8.8 Hz), 4.72 (1H, t, J=8.8 Hz), 5.46 (1H, dd, J=5.1 and 8.8 Hz), 5.75 (1H, q, J=6.8 Hz), 7.37 (5H, s);
Mass m/e: 299, 297 (M$^+$);
Elementary analysis for C$_{12}$H$_{12}$BrNO$_3$:
Calcd.: C, 48.34; H, 4.06; N, 4.70%.
Found: C, 48.27; H, 3.97; N, 4.61%.

EXAMPLE 4-(2)

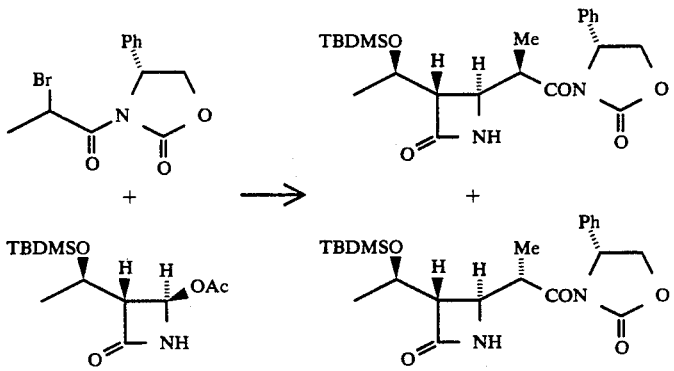

To a solution of (4R)-3-(2'-bromopropionyl)-4-phenyloxazolidin -2-one (236 mg; 0.792 mmol) and (1'R,3R,4R) -3-[1'-(t-butyldimethylsilyloxy)ethyl]-4-acetoxyazetidin-2-one (114 mg; 0.397 mmol) in dry tetrahydrofuran, zinc powder (77 mg) was added at 0° C. After vigorous stirring of the mixture for 30 minutes, a phosphate buffer (pH 7) (2.4 ml) was added thereto to decompose the excess reaction agent. The reaction mixture was extracted with ethyl acetate. The organic layer was dried over anhydrous magnesium sulfate, and the solvent was distilled off under reduced pressure to give the residue, which was purified by silica gel column chromatography to give a mixture (7:13) of (1'R,1''R,3S,4R,4'''R) and (1'R,1S, 3S,4R,4R)-3-[1-(t-butylethyl]-4-[1''-(4'''-phenyloxazolidin-2'''-one -3'''-carbonyl)ethyl]azetidin-2-one (176 mg, yield, 99%).

Two isomers were separated by medium pressure column chromatography on silica gel (dichloromethane:acetone=97:3).

Analysis Data (1'R,1''R,3S,4R,4'''R)-form, colorless caramel:
$[\alpha]^{20}_D -70.4°$ (c=0.66, CHCl$_3$);
IR (KBr): 2950, 1783, 1709, 1460, 1388, 1330, 1255, 1201, 1110, 1047, 962, 840, 781, 703 cm$^{-1}$;
H-NMR δ(CDCl$_3$) 0.11 (6H, s), 0.91 (9H, s), 1.20 (3H, d, J=7.0 Hz), 1.24 (3H, d, J=6.2 Hz), 3.05 (1H, m), 3.98 (1H, m), 4.07–4.37 (2H, m), 4.76 (1H, t, J=8.8 Hz), 5.50 (1H, m), 5.90 (1H, bs), 7.40 (5H, m);
Mass m/e: 389 (M-57)$^+$;
Elementary analysis for C$_{23}$H$_{34}$N$_2$O$_5$Si:
Calcd.: C, 61.85; H, 7.67; N, 6.27%.
Found: C, 61.82; H, 7.91; N, 6.24%.
(1'R,1''S,3S,4R,4'''R)-form, colorless caramel:
$[\alpha]^{20}_D -5.3°$ (c=1.37, CHCl$_3$);
IR (KBr): 2950, 1781, 1703, 1460, 1388, 1255, 1235, 1200, 1108, 1045, 990, 839, 780, 707 cm$^{-1}$;
H-NMR δ(CDCl$_3$) 0.11 (6H, s), 0.93 (9H, s), 1.23 (3H, d, J=6.4 Hz), 1.35 (3H, d, J=6.4 Hz), 2.87 (1H, bd, J=5.1 Hz), 3.85 (2H, m), 4.14–4.41 (2H, m), 4.78 (1H, t, J=8.8 Hz), 5.48 (2H, m), 7.42 (5H, m);
Mass m/e: 389 (M-57)$^+$;
Elementary analysis for C$_{23}$H$_{34}$N$_2$O$_5$Si:
Calcd.: C, 61.85; H, 7.67; N, 6.27%.
Found: C, 61.64; H, 7.95; N, 6.30%.

REFERENCE EXAMPLE 4-(1)

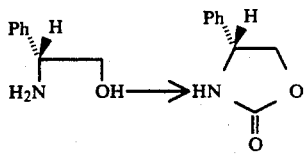

(2R)-2-Amino-2-phenyl-1-ethanol (0.560 g; 4.08 mmol) was treated in the same manner as in Reference example 2-(2) to obtain (4R)-4-phenyloxazolidin-2-one (0.604 g, yield, 91%). The sample for analysis was obtained by recrystallization from toluene. Colorless crystals, M.P., 131°–132° C.

$[\alpha]^{23}_D$ −54.9° (c=1.40, CHCl$_3$);

IR (KBr): 1740, 1710, 1490, 1402, 1236, 1099, 1037, 1024, 970, 921 cm$^{-1}$;

H-NMR δ(CDCl$_3$) 4.19 (1H, dd, J=6.4 and 7.9 Hz), 4.73 (1H, t, J=8.6 Hz), 4.99 (1H, m), 5.40 (1H, bs), 7.37 (5H, s);

Mass m/e: 163 (M+);

Elementary analysis for C$_9$H$_9$NO$_2$:
Calcd.: C, 66.25; H, 5.56; N, 8.58%.
Found: C, 66.08; H, 5.57; N, 8.52%.

REFERENCE EXAMPLE 4-(2)

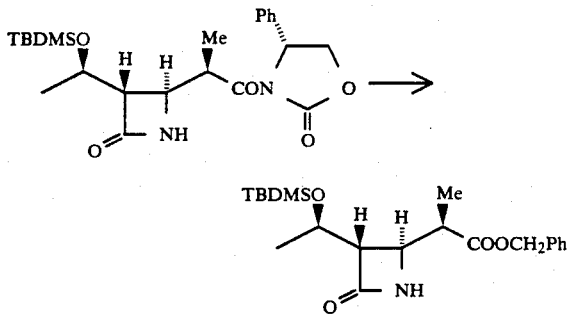

(1'R,1"R,3S,4R,4'''R)-3-[1'-(t-Butyldimethylsilyloxy)ethyl]-4-[1"-(4'''-phenyloxazolidin-2'''-one-3'''-carbonyl)ethyl]azetidin-2-one (14.4 mg) was treated in the same manner as in Reference Example 6-(2)-1 to obtain (1'R,1"R,3S,4S)-3-[1'-(t-butyldimethylsilyloxy)ethyl]-4-[1"-(benzyloxycarbonyl)ethyl]azetidin-2-one (3.4 mg, yield, 27%).

This product was identical with the one obtained in Reference Example 6-(2)-2 in with respect to IR, NMR and Mass spectra in addition to the melting point and the optical rotation.

EXAMPLE 5-(1)

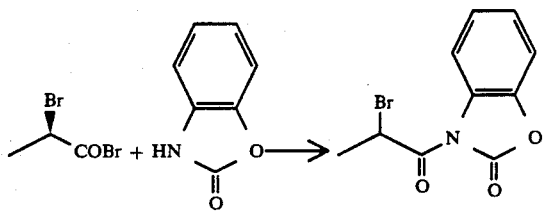

To a solution of benzoxazolidin-2-one (0.371 g; 2.75 mmol) in tetrahydrofuran (5.4 ml), a 1.62 N solution of n-butyl lithium in hexane (1.70 ml; 2.75 mmol) was added at 0° C., followed by adding 2-bromopropionyl bromide (0.290 ml; 2.76 mmol). The mixture was stirred at 0° C. to room temperature for 1 hour, and then a saturated aqueous solution of potassium dihydrogenphosphate (2 ml) was added thereto. After extracting the aqueous layer with ethyl acetate, the organic layer was dried, and the solvent was distilled off under reduced pressure to give a colorless solid (0.923 g). Recrystallization from a mixture of cyclohexane and ethyl acetate (4:1) gave 3-(2'-bromopropionyl)benzoxazolidin-2-one (0.543 g, yield, 73%) as colorless needle-like crystals. M.P., 99°–100° C.

IR (KBr): 1799, 1733, 1488, 1371, 1309, 1255, 1150, 1038, 760 cm$^{-1}$;

H-NMR δ(CDCl$_3$) 1.96 (3H, d, J=6.8 Hz), 5.81 (1H, q, J=6.8 Hz), 7.25 (3H, m), 8.06 (1H, m);

Mass m/e: 271, 269 (M+).

Elementary analysis for C$_{10}$H$_8$BrNO$_3$:
Calcd.: C, 44.47; H, 2.99; N, 5.19%.
Found: C, 44,43, H, 2.79; N, 5.16%.

EXAMPLE 5-(2)

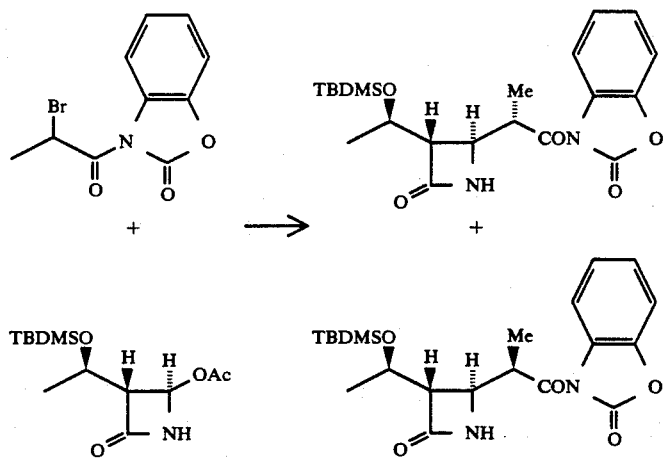

3-(2'-Bromopropionyl)benzoxazolidin-2-one (53.0 mg; 0.196 mmol), (1'R,3R,4R)-3-[1'-(t-butyldimethylsilyloxy)ethyl]-4-acetoxyazetidin-2-one ($[\alpha]^{20}_D$+47.4°, c=1.14, CHCl$_3$) (23.2 mg; 0.081 mmol) and zinc powder (16 mg) were mixed, to which tetrahydrofuran (0.3 ml) was added under ice cooling, and the mixture was vigorously stirred for 30 minutes. With addition of a phosphate buffer (pH 7) (0.4 ml) and dichloromethane (5 ml), the reaction was stopped, and after separation of the organic layer, the residue was dried over anhydrous sodium sulfate, and the solvent was distilled off under reduced pressure. The resulting residue was purified by thin layer chromatography (hexane:ethyl acetate (3:2) to give a mixture of (1'R,1"R,3S,4R)- and (1'R,1"S,3S,4R)-3-[1'-(t-butyldimethylsilyloxy)ethyl]-4-[1"-(benzoxazolidin-2"'-one-3"'-carbonyl)ethyl]azetidine-2-one (22.2 mg, yield, 65%) as a colorless caramel.

The formation ratio of (1'R,1"R,3S,4R)-form to (1'R,1"S,3S,4R)-form was determined as approximately 1:1 from the NMR data.

IR (KBr): 2950, 1801, 1762, 1726, 1488, 1307, 1283, 1253, 1142, 1029, 838 cm$^{-1}$;

H-NMR δ(CDCl$_3$) 0.08 (6H, s), 0.88 (9H, s), 2.94 (0.5H*α, m), 3.12 (0.5H*β, m), 6.10 (1H, bs);

*α: signal of (1"S)-form; *β:signal of (1"R)-form.
Mass m/e: 361 (M-57)$^+$.

EXAMPLE 6-(1)-1

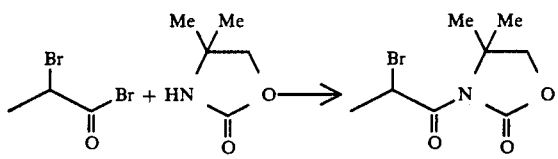

To a solution of 4,4-dimethyloxazolidin-2-one (0.384 g; 3.34 mmol) in tetrahydrofuran (13 ml), a 1.60 N solution of n-butyl lithium in hexane (2.09 ml; 3.34 mmol) was added at 0° C., after which 2-bromopropionyl bromide (0.384 ml; 3.66 mmol) was added thereto. The mixture was stirred at 0° C. overnight, and a saturated aqueous solution of sodium hydrogencarbonate (3.0 ml) was added thereto. The organic layer was dried over anhydrous sodium sulfate, and the solvent was distilled off under reduced pressure. The resulting solid was purified by silica gel column chromatography (hexane:dichloromethane=1:1~0:1) to give 3-(2'-bromopropionyl)-4,4-dimethyloxazolin-2-one (0.701 g, yield, 84%) as a colorless solid. The sample for analysis was recrystallized from cyclohexane. Colorless needle-like crystals. M.P., 73°-74° C.

IR (KBr): 3030, 1775, 1709, 1370, 1310, 1183, 1105, 1069, 760, 702 cm$^{-1}$;

H-NMR δ(CDCl$_3$):1.58 (3H, s), 1.60 (3H, s), 1.81 (3H, d, J=6.8 Hz), 4.06 (2H, s), 5.74 (1H, q, J=6.8 Hz);

Mass m/e: 251, 249 (M)$^+$, 170 (M-80)$^+$;

Elementary analysis for C$_8$H$_{12}$BrNO$_3$:
Calcd.: C, 38.42; H, 4.84; N, 5.60%.
Found: C, 38,39; H, 4.72; N, 5.53%.

EXAMPLE 6-(1)-2

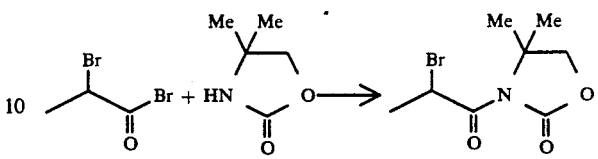

To a suspension of sodium hydride (0.24 g; 10.0 mmol) in tetrahydrofuran (100 ml) was added 4,4-dimethyloxazolidin-2-one (1.15 g; 10.0 mmol) at 0° C., and the resultant suspension was stirred at room temperature for 5 hours. To the gelatinous reaction mixture was added 2-bromopropionyl bromide (1.05 ml) at 0° C. After stirring for 1 hour, a saturated aqueous solution of potassium dihydrogen phosphate was added to quench the reaction. An aqueous layer was extracted with ethyl acetate. Combined organic layers were dried over anhydrous sodium sulfate, and the solvent was distilled off under reduced pressure to give a solid residue, which was purified by silica gel column chromatography (hexane:dichloromethane=1:1~0:1) to give 3-(2'-bromopropionyl)-4,4-dimethyloxazolidin-2-one (2.35 g, yield, 90%) as colorless crystals.

This product was identical with the one obtained in Example 6-(1)-1 in with respect to IR, NMR and Mass spectra in addition to the melting point.

EXAMPLE 6-(2)-1

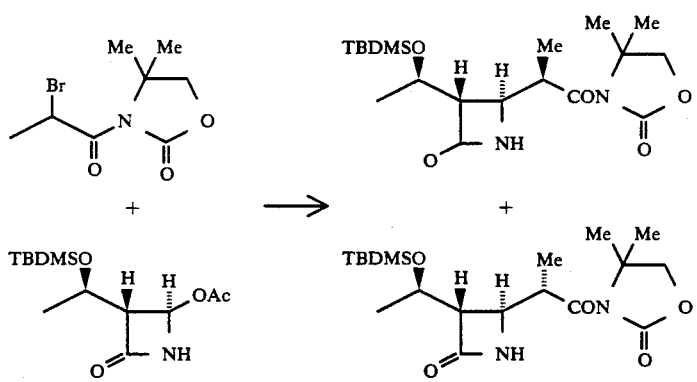

A solution of 3-(2'-bromopropionyl)-4,4-dimethyloxazolidin-2-one ((24.4 mg; 0.098 mmol), (1'R,3R,4R)-3-[1'-(t-butyldimethylsilyloxy)ethyl]-4-acetoxyazetidin-2-one (14.0 mg; 0.049 mmol) in tetrahydrofuran (0.5 ml) was heated at 70° C. Zinc powder (10 mg; 0.15 mmol) was added to the refluxing solution and then stirred for 1 minute. The reaction mixture was cooled to room temperature, diluted with dichloromethane (10 ml) and washed with a phosphate buffer (0.3 ml). The organic layer was dried over anhydrous magnesium sulfate, and the solvent was distilled off under reduced pressure to give the residue, which was purified by silica gel column chromatography (dichloromethane→dichloromethane:ethyl acetate=4:1) to give a mixture of (1'R,1"R,3S,4R) and (1'R,1"S,3S,4R)-3-[1'-(t-butyldimethylsilyloxy)ethyl]-4-[1"-(4"',4"'-dimethyloxazolidin-2"'-one-3"'-carbonyl)ethyl]azetidin-2-one (18.4 mg, yield, 94%) as a colorless solid. The formation ratio of (1'R,1"R,3S,4R)-form to (1'R,1"S,3S,4R)-form was determined to be 79:21 from the H-NMR spectrum.

IR (KBr): 2950, 1762, 1713, 1460, 1380, 1310, 1227, 1184, 1096, 1051, 840, 780 cm$^{-1}$;

H-NMR δ(CDCl$_3$): 0.06 (6H, s), 0.86 (9H, s), 1.55 (6H, s), 2.79 (0.37H*$^α$, dd, J=5.3 and 1.1 Hz), 3.00 (0.63H*$^β$, m), 4.00 (2H, s), 5.90 (1H, bs);

*α:signal of (1"S)-form; *β:signal of (1"R)-form.
Mass m/e: 341 (M-57)$^+$.

EXAMPLE 6-(2)-3

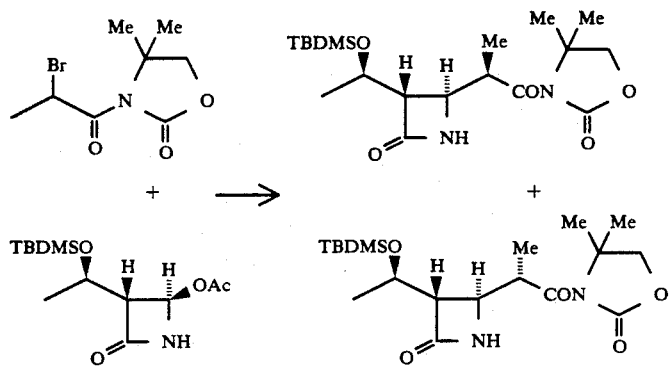

A solution of 3-(2'-bromopropionyl)-4,4-dimethyloxazolidin-2-one (25.9 mg; 0.104 mmol) and (1'R, 3R, 4R)-3-[1'-(t-butyldimethylsilyloxy)ethyl]-4-acetoxyazetidin-2-one (14.9 mg; 0.052 mmol) in dimethoxyethane (0.5 ml) was heated at 70° C. Zinc powder (10 mg; 0.15 mmol) was added to the solution while stirring for 1 minute. The reaction mixture was treated in the same manner as in Example 6-(2)-1 to give a mixture of (1'R, 1"R, 3R, 4R)-and (1'40 R,1"S,3S,4R)-3-[1'-(t-butyldimethylsilyloxy)ethyl]-4-[1'''-(4''',4'''-dimethyloxazolidin-2'''-one-3'''-carbonyl)ethyl]azetidin-2-one (19.9 ms, yield, 96%) as a colorless solid.

The formation ration of (1'R,1"R,3S,4R)-form to (1'R,1"S,3S,4R)-form was determined to be 81:19 by H-NMR spectrum.

Two isomers were separated by medium pressure column chromatography on silica gel (n-hexane:dichloromethane:diethyl ether=10:3:7~1:1:1), and each isomer was recrystallized from n-hexane and ethyl acetate.

Analysis Data (1'R,1"R,3S,4R)-form, M.P., 189°-190° C.
[α]$^{20}_D$−19.2° (c=2.02, CHCl$_3$);

IR (KBr): 2950, 1760, 1717, 1460, 1400, 1386, 1342, 1312, 1228, 1186, 1087, 1054, 960, 840, 781, 770 cm$^{-1}$;

H-NMR δ(CDCl$_3$):0.07 (6H, s), 0.87 (9H, s), 1.19 (3H, d, J=6.8 Hz), 1.21 (3H, d, J=6.2 Hz), 1.56 (6H, s), 3.01 (1H, m), 3.90 (1H, m), 4.01 (2H, s), 4.17 (3H, m), 5.87 (1H, bs);

Mass m/e: 341 (m-57)$^+$;
Elementary analysis for C$_{19}$H$_{34}$N$_2$O$_5$Si:
Calcd.: C, 57.26; H, 8.60; N, 7.03%.
Found: C, 57.31; H, 8.50; N, 6.99%.
(1'R,1"S,3S,4R)-form, M.P., 176°-177° C.:

[α]$^{20}_D$+31.4° (c=1.09, CHCl$_3$);
IR (KBr): 2980, 1780, 1767, 1702, 1380, 1305, 1223, 1178, 1100, 1045, 962, 839, 778 cm$^{-1}$;

H-NMR δ(CDCl$_3$):0.08 (6H, s), 0.89 (9H, s), 1.25 (3H×2, d, J=6.3 Hz), 1.56 (6H, s), 2.81 (1H, dd, J=5.2 and 1.0 Hz), 3.72 (1H, m), 4.03 (2H, s), 4.20 (1H, m), 5.81 (1H, bs);

Mass m/e: 341 (m-57)$^+$;
Elementary analysis for C$_{19}$H$_{34}$N$_2$O$_5$Si:
Calcd.: C,57.26; H, 8.60; N, 7.03%.
Found: C, 57.29; H, 8.51; N, 6.96%.

EXAMPLE 6-(2)-3

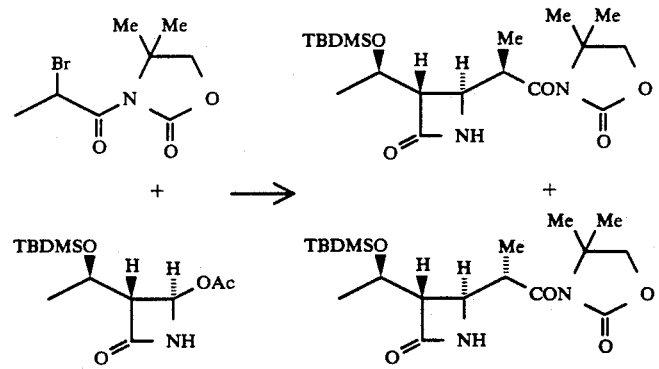

A suspension of zinc powder (2.04 g) in tetrahydrofuran (12 ml) was heated under reflux. A solution of -(2'-bromopropionyl)-4,4-dimethyloxazolidin-2-one (5.22 g) and (1'R,3R,4R)-3-[1'-(t-butyldimethylsilyloxy)ethyl]-4-acetoxyazetidin-2-one (3.0 g) in tetrahydrofuran (18 ml) was added to the suspension, followed by stirring for 30 minutes under reflux. The reaction mixture was cooled to room temperature, and the solvent was distilled off under reduced pressure. To the resulting residue, acetic acid (0.63 g) and dichloromethane (10 ml) were added, followed by stirring. After filtration, the filtrate was successively washed with 3.6% hydrochloric acid, water and a 5% aqueous solution of sodium bicarbonate, and then dried over anhydrous magnesium sulfate. The solvent was distilled off under reduced pressure to give the residue, which was crystallized from n-heptane to give a mixture of (1'R,1"R,3S,4R)- and (1'R,1"S,3S,4R)-3-[1'-(t-butyldimethylsilyloxy)ethyl]-4-[1"-(4''',4'''-dimethyloxazolidin-2'''-one-3'''-carbonyl)ethyl]azetidin-2-one (3.95 g, yield, 95%) as a colorless solid. The formation ratio of (1'R,1"R,3S,4R)-form to (1'R,1"S,3S,4R)-form was determined to be 81:19 by the H-NMR spectrum.

EXAMPLES 6-(2)-4 to 6-(2)-16

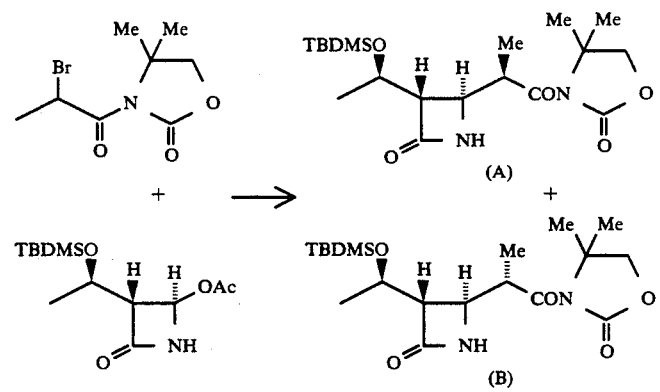

In the same manner as in Example 6-(2)-1, there were obtained mixtures of beta-lactam derivatives (1'R,1"R,3S,4R)-form (A)] and [(1'R,1"S,3S,4R)-form (B)] from 4-acetoxyazetidin-2-one derivative. The reaction conditions and the results are shown in Table 1.

TABLE 1

| Example No. | Reaction condition | | | | Yield (%) | Ratio of (A):(B) | Remarks |
|---|---|---|---|---|---|---|---|
| | Time (min) | Temp. (°C.) | Solvent* | Metal | | | |
| 6-(2)-4 | 120 | −20~−15 | THF | Zn | 45 | 50:50 | 23% material recovered |
| 6-(2)-5 | 30 | 0 | THF | Zn | 90 | 63:37 | |
| 6-(2)-6 | 10 | 25 | THF | Zn | 90 | 77:23 | |
| 6-(2)-7 | 10 | 25 | THF | Zn | 75 | 77:23 | 1.2 Equivalent amounts of reaction agent used; 13% material recovered |
| 6-(2)-8 | 180 | 0 | Et₂O | Zn | 81 | 66:34 | |
| 6-(2)-9 | 10 | 25 | DMF | Zn | 80 | 69:31 | 20% material recovered |
| 6-(2)-10 | 1 | 100 | 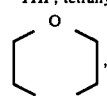 | Zn | 20 | 80:20 | |
| 6-(2)-11 | 10 | 25 | 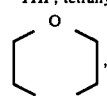 | Zn | 99 | 62:23 | |
| 6-(2)-12 | 1 | 70 | 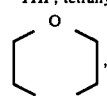 | Zn | 99 | 78:22 | |
| 6-(2)-13 | 10 | 25 | DME | Zn | 88 | 62:28 | 11% material recovered |
| 6-(2)-14 | 1 | 85 | DME | Zn | 70 | 83:17 | |
| 6-(2)-15 | 60 | 80 | Toluene | Zn | 45 | 71:29 | |
| 6-(2)-16 | 5 | 25 | THF | Mg | 34 | 80:20 | |

Note:
*THF, tetrahydrofuran; Et₂O, diethyl ether; DMF, dimethylformamide,

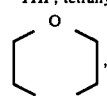, dioxane; DME, 1,2-dimethoxyethane.

EXAMPLE 6-(3)

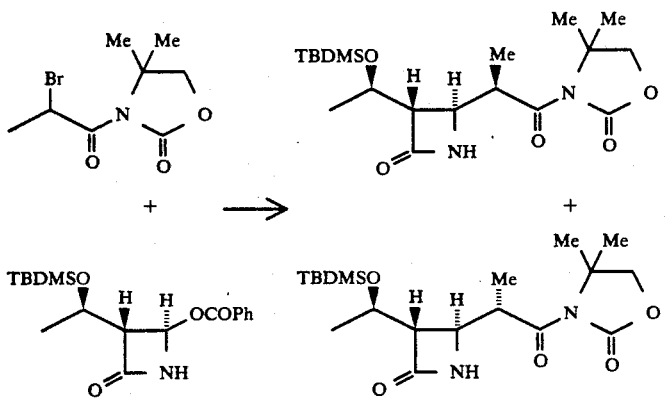

In the same manner as in Example 6-(2)-1, there was obtained a mixture of (1'R,1"R,3S,4R)- and (1'R,1"R,3S,4R)-3-[1'-(t-butyldimethylsilyloxy)ethyl]-4-[1"-(4''',4'''-dimethyloxazolidin-2'''-one-3'''-carbonyl)ethyl]azetidin-2-one from (1'R,3R,4R)-3-[1'-(t-butyldimethylsilyloxy)ethyl]-4-benzoyloxyazetidin-2-one and 3-(2'-bromopropionyl)-4,4-dimethyloxazolidin-2-one.

REFERENCE EXAMPLE 6-(1)

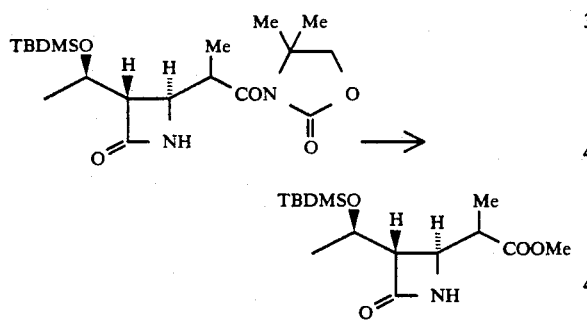

A mixture of (1'R,1"R,3S,4R)- and (1'R,1"S,3S,4R)-3-[1'-(t-butyldimethylsilyloxy)ethyl]-4-[1"-(4''', 4'''-dimethyloxazolidin-2'''-one-3'''-carbonyl)ethyl]azetidin-2-one prepared in Example 6-(2)-1 (11.1 mg; 0.028 mmol) was dissolved in dry methanol (0.3 ml), to which anhydrous potassium carbonate (19.0 mg; 0.13 mmol) was added, and the mixture was vigorously stirred at room temperature for 30 minutes. A saturated aqueous solution of potassium dihydrogen phosphate was added to quench the reaction and dichloromethane was added thereto. The organic layer was dried over anhydrous sodium sulfate, and the solvent was distilled off to give a colorless solid, which was purified by thin layer chromatography (ether:hexane=9:1) to give (1'R,1"R,3S,4S)-3-[1'-(t-butyldimethylsilyloxy)ethyl]-4-[1"-(methoxycarbonyl)ethyl]azetidin-2-one (1.4 mg, yield, 16 %) as a colorless solid.

This product was identical with the one obtained in Reference Example 1 with respect to IR, NMR and Mass spectra in addition to the melting point and the optical rotation.

REFERENCE EXAMPLE 6-(2)-1

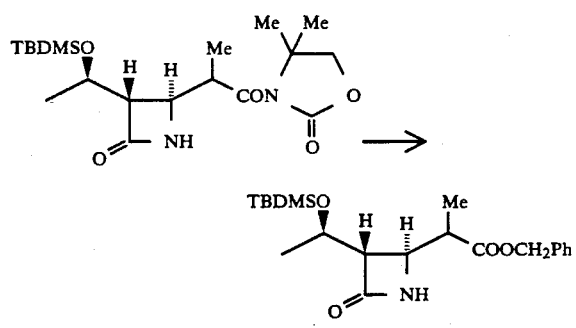

A mixture of (1"R)-form and (1"S)-form of (1'R,3S,4R)-3-[1'-(t-butyldimethylsilyloxy)ethyl]-4-[1"-(4''',4'''-dimethyloxazolidin-2'''-one-3'''-carbonyl)ethyl]azetidin-2-one prepared in Example 6-(2)-1 (mixing ratio, 79:21) (30.3 mg; 0.076 mmol) was dissolved in tetrahydrofuran (0.4 ml), to which a 0.5 M solution of lithium benzylalkoxide in tetrahydrofuran (0.3 ml) was added with icecooling. After stirring at the same temperature for 1 hour, a saturated aqueous solution of potassium dihydrogen phosphate (0.3 ml) was added to the mixture to quench the reaction, followed by extraction with dichloromethane. The organic layer was dried over anhydrous magnesium sulfate and the solvent was distilled off to give an oily residue, which was purified by silica gel column chromatography (dichloromethane→dichloromethane:ethyl acetate=4:1) to give a mixture of (1'R,1"R,3S,4S)- and (1'R,1"S,3S,4S)-3-[1'-(t-butyldimethylsilyloxy)ethyl]-4-[1"-(benzyloxycarbonyl)ethyl]azetidin-2-one (28.1 mg; yield, 94 %) as a colorless solid.

REFERENCE EXAMPLE 6-(2)-2

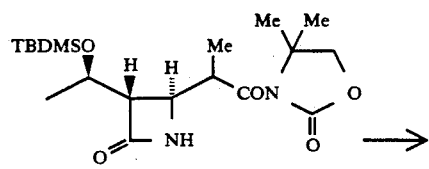

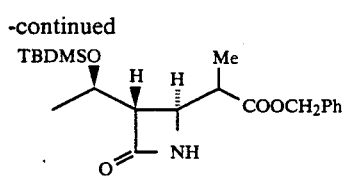

To a solution of (1′R,1″R,3S,4R)-3-[1′-(t-butyldimethylsilyloxy)ethyl]-4-[1″-(4‴,4‴-dimethyloxazolidin‴-one-3‴-carbonyl)ethyl]azetidin-2-one (76.6 mg; 0.192 mmol) in tetrahydrofuran (0.96 ml) was added a 0.5 M solution of lithium benzylalkoxide in tetrahydrofuran (0.77 ml) at 0° C., and the resultant mixture was stirred for 1 hour at the same temperature. The reaction mixture was treated in the same manner as in Reference Example 6-(2)-1 to give (1′R,1″R,3S,4S)-3-[1′-(t-butyldimethylsilyloxy)ethyl]-4-[1″-(benzyloxycarbonyl)ethyl]azetidin-2-one (74.1 mg, yield, 98%) as colorless crystals. M.P., 69°–70° C.

$[\alpha]^{25}_D$ −13.8° (c=0.98, CHCl$_3$);

IR (KBr): 2950, 1769, 1738, 1719, 1460, 1380, 1353, 1340, 1257, 1177, 1138, 1105, 1068, 1048, 961, 840, 782, 736, 698 cm$^{-1}$;

H-NMR δ (CDCl$_3$): 0.11 (6H, s), 0.91 (9H, s), 1.18 (3H, d, J=6.4 Hz), 1.29 (2H, d, J=7.0 Hz), 2.79 (1H, m), 3.01 (1H, m), 3.96 (1H, m), 4.22 (1H, m), 5.17 (2H, s), 5.91 (1H, bs), 7.39 (5H, s);

Mass m/e: 334 (M-57)$^+$;

Elementary analysis for C$_{21}$H$_{33}$NO$_4$Si:

Calcd.: C, 64.41; H, 8.49; N, 3.58%.

Found: C, 64.42; h, 8.33; N, 3.61%.

REFERENCE EXAMPLE 6-(2)-3

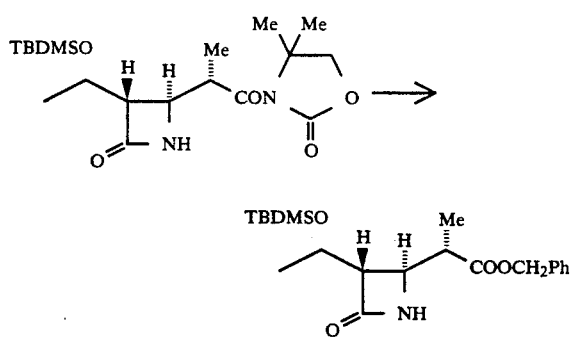

In the same manner as in Reference Example 6-(2)-1, there was obtained as an oil (1′R,1″S,3S,4S)-3-[1′-(t-butyldimethylsilyloxy)ethyl]-4-[1″-(benzyloxycarbonyl)ethyl]azetidin-2-one (21.5 mg, yield, 95%) from (1′R,1″S,3S,4R)-3-[1′-(t-butyldimethylsilyloxy)ethyl]-4″-(4‴,4‴-dimethyloxazolidin-2‴-one-3‴-carbonyl)ethyl]-azetidin-2-one (23.1 mg; 0.058 mmol).

$[\alpha]^{25}_D$ +3.01° (c=1.59, CHCl$_3$);

IR (neat): 2950, 1763, 1739, 1460, 1256, 1183, 1143, 1100, 1043, 960, 833, 778, 698 cm$^{-1}$;

H-NMR δ (CDCl$_3$) 0.07 (6H, s), 0.88 (9H, s), 1.23 (3H, d, J=6.0 Hz), 1.25 (3H, d, J=7.3 Hz), 2.58 (1H, dq, J=9.5 and 7.3 Hz), 2.76 (1H, m), 3.71 (1H, dd, J=9.5 and 2.0 Hz), 4.17 (1H, quint, J=6.0 Hz), 5.15 (2H, s), 5.96 (1H, bs), 7.35 (5H, s);

Mass m/e: 376 (M-15)$^+$, 334 (M-57)$^+$.

REFERENCE EXAMPLE 6-(3)

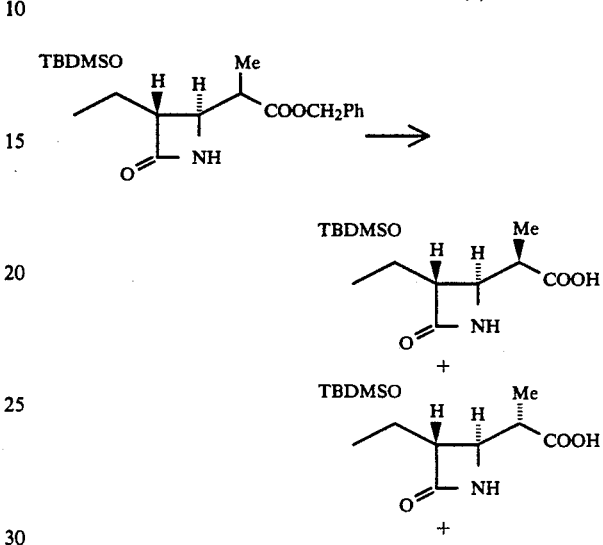

A mixture of (1′R,1″R,3S,4S)- and (1′R,1″S,3S,4 S)-3-[1′-(t-butyldimethylsilyloxy)ethyl]-4-(1″-(benzyloxycarbonyl)ethyl]azetidin-2-one prepared in Reference Example 6-(2)-1 (25.5 mg) was dissolved in ethyl acetate (1 ml), to which 10% palladium carbon (3 mg) was added, and the mixture was stirred at room temperature under hydrogen atmosphere (normal pressure) for 4 hours. Filtration of the catalyst through a celite column and removal of the solvent under reduced pressure gave a solid, which was purified by silica gel column chromatography (dichloromethane:ethyl acetate:acetic acid=3:1:0.02). From the less polar fraction, there was obtained (1′R,1″R,3S,4S)-3-[1′-(t-butyldimethylsilyloxy)ethyl]-4-(1″-carboxyethyl]azetidin -2-one (14.1 mg, yield, 72%). Recrystallization from a mixed solvent of cyclohexane and ethyl acetate gave a pure sample as colorless crystals.

This product was identical with the one obtained in Reference Example 3-(1) in respect to IR, H-NMR and Mass spectra.

Further, from the more polar fraction there was obtained (1′R,1″S,3S,4S)-3-[1′-(t-butyldimethylsilyloxy)ethyl]-4-(1″-carboxyethyl)azetidin-2-one (4.5 mg, yield, 23%). Recrystallization from a mixed solvent of cyclohexane and ethyl acetate gave a pure sample as colorless crystals. M.P., 176°–180° C. (decomp.).

This product was identical with the one obtained in Reference Example 3-(2) in respect to IR, H-NMR and Mass spectra.

EXAMPLE 7

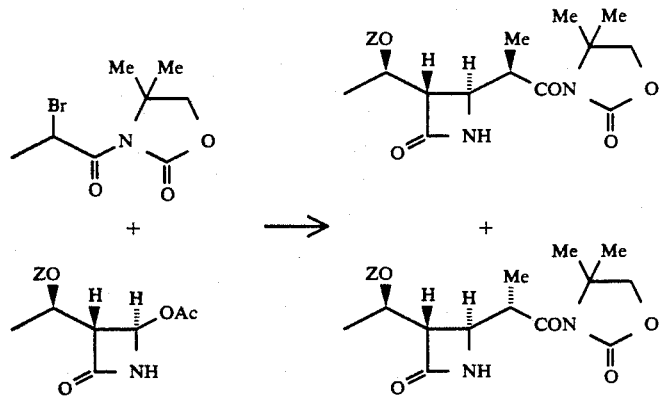

To a suspension of (1'R,3R,4R)-3-[1'-(benzyloxycarbonyloxy)ethyl]-4-acetoxyazetidin-2-one (31.1 g; 0.105 mmol) and zinc powder (20 mg; 0.309 mmol) in tetrahydrofuran (0.9 ml), a solution of 3-(2'-bromopropionyl)-4,4-dimethyloxazolidin-2-one (51 mg; 0.21 mmol) in tetrahydrofuran (0.158 ml) was slowly added at 70° C. After vigorous stirring of the mixture and then cooling to room temperature, a phosphate buffer (pH 7.0) (0.4 ml) was added thereto to decompose the excess reaction agent. The reaction mixture was extracted with dichloromethane (10 ml). The organic layer was dried over anhydrous magnesium sulfate, and the solvent was distilled off under reduced pressure to give the residue, which was purified by silica gel column chromatography to give a mixture of (1'R,1"R,3S,4R)- and (1'R,1"S,3S,4R)-3-[1'-(benzyloxycarbonyloxy)ethyl]-4-[1"-(4''',4'''-dimethyloxazolidin-2''' -one-3'''-carbonyl)ethyl]azetidin-2-one (42.1 mg, yield, 98%).

The formation ratio of (1'R,1"R,3S,4R)-form to (1'R,1"S,3S,4R)-form was determined to be approximately 5:1 by the NMR spectrum.

IR (neat): 3000, 1770, 1700, 1385, 1309, 1265, 1180, 1092, 1040, 700 cm$^{-1}$;

H-NMR δ (CDCl$_3$): 1.16 (3H, d, J=6.8 Hz), 1.42 (3H, d, J=6.4 Hz), 1.53 (6H, s), 3.01 (1/6H*$^α$, m), 3.21 (5/6H*$^β$, m), 4.00 (2H, s), 5.15 (2H, s), 6.15 (1H, bs), 7.35 (5H, s);

*α:signal of (1"S)-form; *β: signal of (1"R)-form.
Mass m/e: 418 (M+).

REFERENCE EXAMPLE 7-(1)

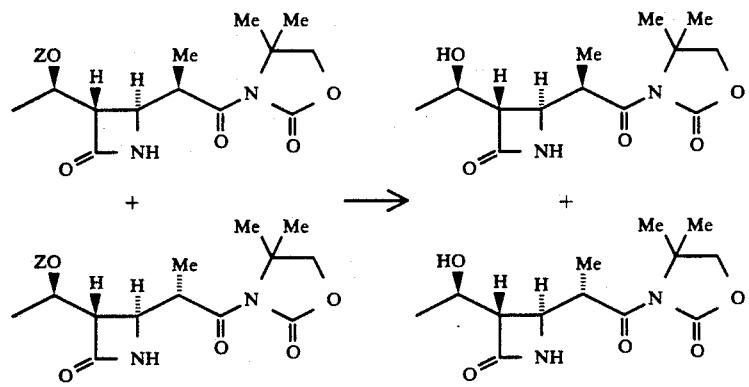

A mixture of (1'R,1"R,3S,4R)-form and (1'R,1"S,3S,4R)-3-[1'-(benzyloxycarbonyloxy)ethyl]-4-[1" -(4''',4'''-dimethyloxazolidin-2'''-one-3'''-carbonyl)ethyl]-azetidin-2-one prepared in Example 7 (mixing ratio, about 5:1) (42.0 mg) was dissolved in ethyl acetate (3.0 ml), to which 10% palladium carbon (2 mg) was added, and the mixture was stirred under a hydrogen atmosphere (normal pressure) at room temperature for 4 hours. The catalyst was removed by filtration through a celite column, and the filtrate was evaporated under reduced pressure to give a mixture of (1'R,1"R,3S,4R)- and (1'R,1"S,3S,4R)-3-(1'-hydroxyethyl) -4-[1"-(4''',4'''-dimethyloxazolidin-2'''-one-3'''-carbonyl)ethyl]azetidin-2-one (29.0 mg, quantitative yield). This product was used for the next reaction without purification.

REFERENCE EXAMPLE 7-(2)

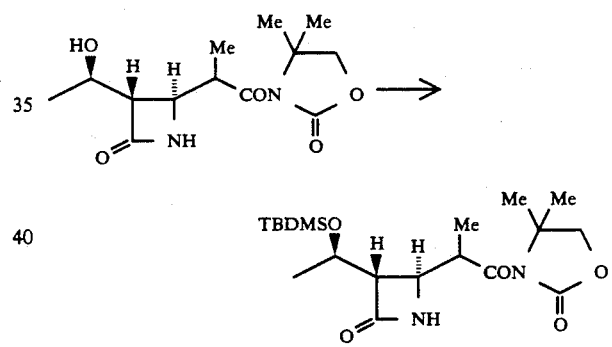

To a solution of 3-(1'-hydroxyethyl)-4-[1"-(4''',4'''-dimethyloxazolin-2'''-one-3'''-carbonyl)ethyl]-azetidin-2-one (29.0 mg) obtained in Reference Example 7-(1) in dry dimethylformamide (1 ml), imidazole (14 mg) and t-butyldimethylchlorosilane (31 mg) were added at room temperature, and the resultant mixture was stirred for 3 hours. To the reaction mixture, ethyl acetate and water were added to quench the reaction. The organic layer was washed with brine and dried over anhydrous magnesium sulfate. The solvent was distilled off under reduced pressure to give a residue, which was purified by silica gel column chromatography (dichloromethane:ethyl acetate=4:1 to give a mixture of (1'R,1"R,3S,4R)- and (1'R,1"S,3S,4R) -3-[1'-(t-butyldimethylsilyloxy)ethyl]-4-[1"-(4''',4'''-dimethyloxazolidin-2'''-one-3'''-carbonyl)ethyl]azetidin-2-one (29.9 mg, yield, 74%) as a colorless solid. The formation ratio of (1'R,1"R,3S,4R)-form to (1'R,1"S,3S,4R)-form was determined to be 4.9:1 by the NMR spectrum. This product was identical with the one obtained in Example 6-(2)-1 in respect to IR, H-NMR and Mass spectra.

EXAMPLE 8-(1)

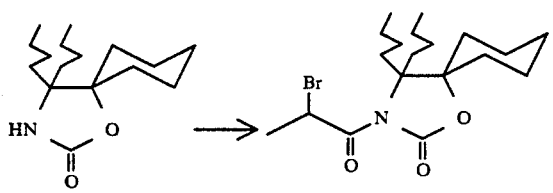

To a solution of 4,4-dibutyl-5,5-pentamethyleneoxazolidin-2-one (2.64 g; 9.9 mmol) in dry diethyl ether (12 ml), a 1.65 N solution of n-butyl lithium in hexane (6.59 ml, 10.9 mmol) was added at 0° C. After 5 minutes, 2-bromopropionyl bromide (1.24 ml; 11.8 mmol) was added, and the resultant mixture was stirred at room temperature for 10 minutes. To the reaction mixture, a phosphate buffer (pH 7) (5.0 ml) was added to decompose the excess reaction agent. The organic layer was washed with an aqueous solution of sodium bicarbonate and then brine and dried over anhydrous magnesium sulfate. The solvent was distilled off under reduced pressure to give a residue, to which methanol (4.5 ml) was added and followed by heating. Hot methanol solution was gradually cooled to give 3-(2'-bromopropionyl)-4,4-dibutyl-5,5-pentamethyleneoxazolidin-2-one (2.4 g, yield, 63%) as colorless crystals. M.P., 113°-114° C.

IR (KBr): 2960, 2880, 1761, 1710, 1450, 1375, 1360, 1290, 1275, 1255, 1240, 1180, 1113, 1060, 990, 960, 881, 770, 720, 643, 540 cm$^{-1}$;

H-NMR δ (CDCl$_3$): 0.75-1.10 (6H, m), 1.1-1.5 (10H, m), 1.5-2.5 (12H, m), 1.81 (3H, d, J=6.8 Hz), 5.87 (1H, q, J=6.8 Hz);

Mass m/e: 346, 344 (M-57)$^+$, 210 (M-191)$^+$;
Elementary analysis for C$_{19}$H$_{32}$BrNO$_3$:
Calcd.: C, 56,72; H, 8.02; N, 3.48; Br, 19.86%.
Found: C, 56.66; H, 8.09; N, 3.43; Br, 19.57%.

EXAMPLE 8-(2)

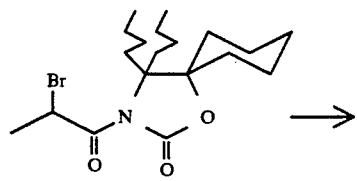

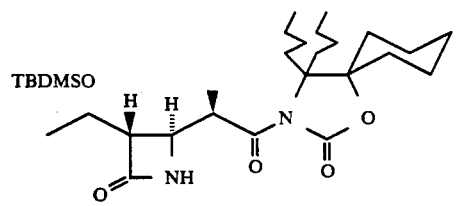

To a suspension of (1'R,3R,4R)-3-[1'-(t-butyldimethylsilyloxy)ethyl]-4-acetoxyazetidin-2-one (135 mg; 0.47 mmol) and zinc powder (113 mg; 1.7 mmol) in tetrahydrofuran (1.9 ml), a solution of 3-(2'-bromopropionyl)4,4-dibutyl-5,5-pentamethyleneoxazolidin-2-one (417 mg; 1.04 mmol) in tetrahydrofuran (1.9 ml) was dropwise added under reflux. After 2 minutes, the reaction mixture was cooled to room temperature, and a phosphate buffer (2.0 ml) and ethyl acetate (50 ml) were added thereto. The organic layer was washed with brine and dried over anhydrous magnesium sulfate. The solvent was distilled off under reduced pressure to give a residue, which was purified by silica gel column chromatography (n-hexane:dichloromethane=1:1→n-hexane:dichloromethane:ethyl acetate=7:1:3) to give a mixture of (1'R,1"R,3S,4R)- and (1'R,1"S,3S,4R)-3-[-1'-(t-butyldimethylsilyloxy)ethyl]-4-[1"-(4''',4'''-dibutyl5''',5'''-pentamethyleneoxazolidin-2'''-one-3'''-carbonyl)ethyl]azetidin-2-one (259 mg, quantitative yield) as a colorless solid. This product was recrystallized from methanol (1.5 ml) to afford (1'R,1"R,3S,4R)-isomer (221 mg; yield, 85%) as colorless crystals. M.P., 158°-159° C.

[α]$^{20}$$_D$−5.0° (c=1.29, CHCl$_3$);

IR (KBr): 3450, 2960, 2900, 1780, 1768, 1714, 1380, 1280, 1240, 1108, 1053, 970, 840, 782 cm$^{-1}$;

H-NMR δ (CDCl$_3$): 0.07 (6H, s), 0.87 (9H, s), 0.90 (6H, m), 1.20 (3H, d, J=6.9 Hz), 1.22 (3H, d, J=6.3 Hz), 1.0-2.2 (22H, m), 3.05 (1H, m), 3.92 (1H, m), 4.11-4.30 (2H, m), 5.88 (1H, bs);

Mass m/e: 493 (M-57)$^+$;
Elementary analysis for C$_{30}$H$_{54}$N$_2$O$_5$Si:
Calcd.: C, 65.41; H, 9.88; N, 5.09%.
Found: C, 65.34; H, 10.06; N, 5.03%.

REFERENCE EXAMPLE 8-(1)

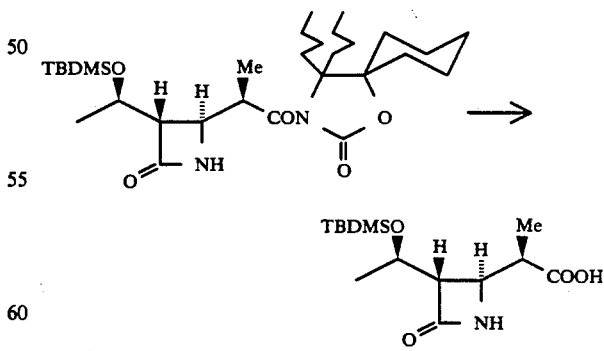

To (1'R,1"R,3S,4R)-3-[1'-(t-butyldimethylsilyloxy)ethyl]-4-[1"-(4''',4'''-dibutyl-5''',5'''-pentamethyleneoxazolidin-2'''-one-3'''-carbonyl)ethyl]azetidin-2-one (54.3 mg; 0.099 mmol), t-butanol (0.37 ml), water (0.104 ml) and a 2N aqueous solution of sodium hydroxide (0.104 ml) were added, and the resultant mixture was stirred at room temperature for 3 days. To the reaction mixture, water (0.8 ml) and n-hexane (4 ml) were added and the organic layer was separated. The aqueous layer was washed with n-hexane (2 ml×2) and then acidified with 1N hydrochloric acid (0.25 ml). The reaction mixture was extracted with ethyl acetate, and the extract was washed with brine and dried over anhydrous magnesium sulfate. The solvent was distilled off under reduced pressure to give a residue, which was purified by silica gel column chromatography to give (1′R,1″R,3S,4S)-3-[1′-(t-butyldimethylsilyloxy)ethyl]-4-(1″-carboxyethyl)azetidin-2-one (27.0 mg, yield, 91%).

The sample for analysis was obtained as colorless crystals by recrystallization from a mixture of n-hexane and ethyl acetate. This product was identical with the one obtained in Reference Example 3-(1) with respect to the melting point, the optical rotation and various spectra of IR, NMR and Mass.

REFERENCE EXAMPLE 8-(2)

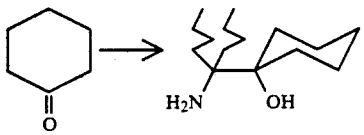

To a mixture of cyclohexanone (6.10 g; 62 mmol) and zinc iodide (1 mg), cyanotrimethylsilane (9.11 ml; 68 mmol) was added with ice-cooling, and the resultant mixture was stirred at room temperature for 1 hour. Excess cyanotrimethylsilane was evaporated under reduced pressure, and the residue was dissolved in anhydrous diethyl ether (60 ml). To the solution, a 1.70 N solution of n-butyl lithium in hexane (82 ml; 139 mmol) was added at 0° C. and followed by stirring at room temperature overnight. The reaction was quenched with 4N hydrochloric acid (100 ml) with stirring at room temperature for 1 hour. An 8N aqueous solution of sodium hydroxide (100 ml) was added thereto at 0° C., and the organic layer was separated. The aqueous layer was extracted with diethyl ether (100 ml×2) and the combined extracts were washed with brine, dried over anhydrous magnesium sulfate and evaporated under reduced pressure to give an oily residue, which was distilled off under reduced pressure to afford 2-amino-2-butyl-1,1-pentamethylene-1-hexanol (13.2 g, yield, 82%) as an oil. The sample for analysis was obtained by alumina column chromatography (n-hexane:diethyl ether=9:1). Colorless oil.

IR (neat): 3420, 2950, 2880, 1588, 1470, 1460, 1447, 1400, 1380, 1261, 1140, 1042, 970, 850 cm$^{-1}$;
H-NMR δ (CDCl$_3$); 0.92 (6H, m), 1.0–2.0 (25H, m);
Mass m/e: 241 (M)$^+$, 224 (M-15)$^+$;
Elementary analysis for C$_{15}$H$_{31}$NO:
Calcd.: C, 74.63; H, 12.94; N, 5.80%.
Found: C, 74.78; H, 12.68; N, 5.67%.

REFERENCE EXAMPLE 8-(3)

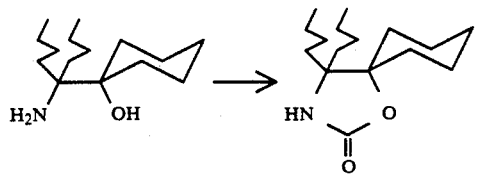

Crude 2-amino-2-butyl-1,1-pentamethylene-1-hexanol (10 g; 41.5 mmol) obtained in Reference Example 8-(2) was dissolved in dry tetetrahydrofuran (40 ml), and the resultant solution was combined with 1,1′-carbonyldiimidazole (13.5 g; 83.3 mmol) and followed by stirring at 65° C. for 4 hours. After cooling to room temperature, an 1N aqueous solution of sodium hydroxide (40 ml) and methanol (30 ml) were added thereto. Stirring was continued at room temperature for 4 hours. The reaction mixture was acidified with conc. hydrochloric acid and extracted with ethyl acetate. The extract was washed with brine and dried over anhydrous magnesium sulfate, and the solvent was distilled off under reduced pressure to give 4,4-dibutyl-5,5-pentamethyleneoxazolidin-2-one (11.0 g, yield, 99%) as a colorless solid. The sample for analysis was obtained by recrystallization from a mixture of methanol and water. Colorless crystals. M.P., 96°–97° C.

IR (KBr): 3240, 3150, 2950, 2880, 1750, 1473, 1378, 1360, 1322, 1280, 987, 950, 880, 735 cm$^{-1}$;
H-NMR δ (CDCl$_3$) 0.91 (6H, t, J=6.3 Hz), 1.0–2.3 (23H, m), 5.89 (1H, bs);
Mass m/e: 268 (M+1)$^+$, 210 (M-57)$^+$;
Elementary analysis for C$_{16}$H$_{29}$NO$_2$:
Calcd.: C, 71.87; H, 10.93; N, 5.24%.
Found: C, 71.95; H, 10.95; N, 5.20%.

EXAMPLE 9-(1)

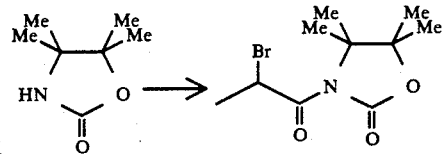

To a solution of 4,4,5,5-tetramethyloxazolidin-2-one (0.30 g; 2.01 mmol) in tetrahydrofuran (2.5 ml), a hexane solution of 1.57 N n-butyl lithium (1.50 ml; 2.3 mmol) was added at 0° C., and after 5 minutes, 2-bromopropionyl bromide (0.54 g; 2.5 mmol) was added thereto and followed by stirring at the same temperature for 10 minutes. A phosphate buffer (pH 7) (1.1 ml) was added thereto to decompose the excess reaction agent, and the reaction mixture was extracted with ethyl acetate. The organic layer was washed with a 5% aqueous solution of sodium bicarbonate and then brine and dried over anhydrous magnesium sulfate. The solvent was distilled off under reduced pressure to give a residue, which was purified by silica gel column chromatography (benzene→benzene:ethyl acetate=95:5) to give 3-(2′-bromopropionyl)-4,4,5,5-tetramethyloxazolidin-2-one as a colorless solid.

IR (Nujol): 1760, 1693, 1300, 1275, 1142, 1083, 1055 cm$^{-1}$.

EXAMPLE 9-(2)

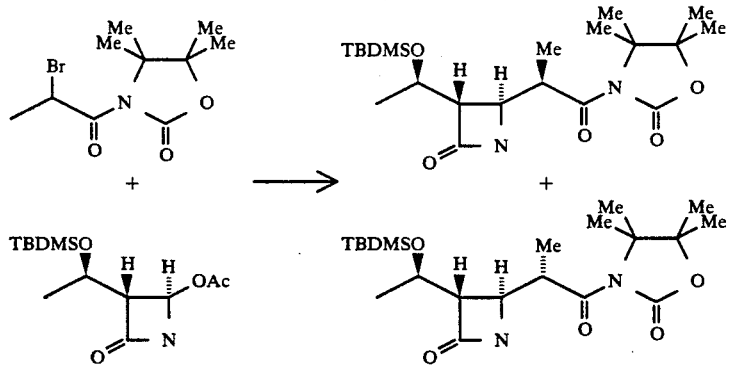

To a suspension of (1'R,3R,4R)-3-[1'-(t-butyldimethylsilyloxy)ethyl]-4-acetoxyazetidin-2-one (68 mg; 0.24 mmol) and zinc powder (57 mg; 0.88 mmol) in tetrahydrofuran (1.0 ml), a solution of 3-(2'-bromopropionyl)-4,4,5,5-tetramethyloxazolidin-2-one (145 mg; 0.52 mmol) in tetrahydrofuran (1.0 ml) was dropwise added under reflux. After 5 minutes, the rection mixture was cooled to room temperature, and a phosphate buffer (1.0 ml) and ethyl acetate were added. The organic layer was successively washed with 1N hydrochloric acid, a 5% aqueous solution of sodium bicarbonate and brine and dried over anhydrous magnesium sulfate. The solvent was distilled off under reduced pressure to give a residue, which was purified by silica gel column chromatography (chloroform:ethyl acetate=9:1) to give a mixture of (1'R,1"R,3S,4R)- and (1'R,1"S,3S,4R)-3-[1'--(t-butyldimethylsilyoxy)ethyl]-4-[1'''-(4''',4''',5''',5'''-tetramethyloxazolidin-2'''-one-3'''-carbonyl)ethyl]azetidin-2-one.

The formation ratio of (1'R,1"R,3S,4R)-form to (1'R,1"S,3S,4R)-form was determined to be 87:13 by the NMR spectrum.

IR (Nujol): 3150 (broad), 1758, 1700, 1335, 1300, 1273 cm$^{-1}$;

H-NMR δ (CDCl$_3$) 0.06 (3H, s), 0.07 (3H, s), 0.87 (0.87×9H*$^\beta$, s), 0.88 (0.13×9H*$^\alpha$, s), 1.36 (6H, s), 1.43 (6H, s), 2.81 (0.13H*$^\alpha$, s), 3.01 (0.87 H*$^\beta$, m), 3.91 (0.87H*$^\beta$, dd, J=2.0 and 4.0 Hz), 5.88 (1H, bs);

*α: signal of (1"S)-form; *δ: signal of (1"R)-form.

REFERENCE EXAMPLE 9

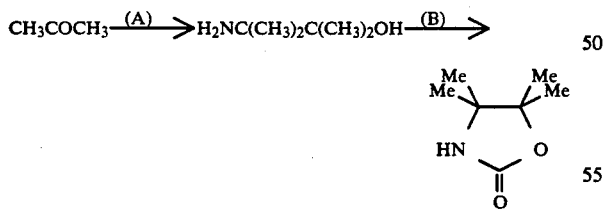

(A) To a mixture of cyanotrimethylsilane (4.1 ml; 31 mmol) and zinc iodide (1 mg), acetone (2.3 ml; 31 mmol) was added with ice-cooling and followed by stirring at room temperature for 1 hour. To the reaction mixture, dry diethyl ether (10 ml) and then a 1.07 N solution of methyl lithium in diethyl ether (64 ml; 68 mmol) were added at 0° C. and stirring was continued at room temperature overnight. After addition of a 30% aqueous solution of sodium hydroxide (50 ml) with ice-cooling, the organic layer was separated. The aqueous layer was extracted with diethyl ether, and the extract was dried over anhydrous magnesium sulfate. The solvent was distilled off under reduced pressure to give 2-amino-1,1,2-trimethyl-1-propanol, which was used without purification for the next reaction.

(B) Crude 2-amino-1,1,2-trimethyl-1-propanol as obtained above (about 6 mmol) was dissolved in tetrahydrofuran (10 ml), and 1,1'-carbonyldiimidazole (3.24 g; 20 mmol) was added thereto while stirring at 65° C. for 4 hours. After cooling to room temperature, an aqueous solution of 1N sodium hydroxide (10 ml) and methanol (7.5 ml) were added thereto and followed by stirring at the same temperature for 4 hours. The reaction mixture was acidified with conc. hydrochloric acid (5 ml) and extracted with ethyl acetate. The extract was washed with brine and dried over anhydrous magnesium sulfate. The solvent was distilled off under reduced pressure to give a residue, which was purified by silica gel column chromatography (chloroform→chloroform:ethyl acetate=9:1) to give 4,4,5,5-tetramethyloxazolidin-2-one as a colorless solid.

IR (Nujol): 3370, 3250, 1755, 1720, 1178, 1022 cm$^{-1}$;

H-NMR δ (CDCl$_3$) 1.25 (6H, s), 1.37 (6H, s), 5.77 (1H, bs).

EXAMPLE 10

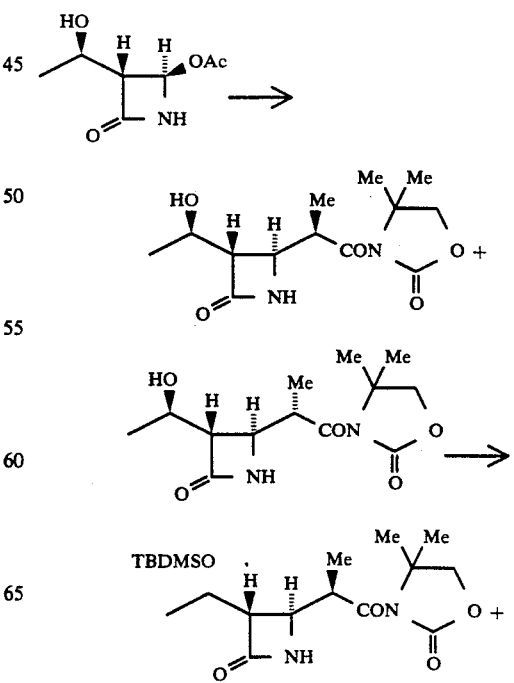

-continued

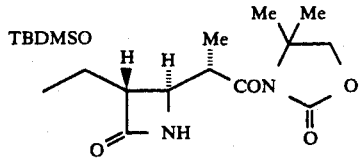

To a suspension of zinc powder (65 mg; 1.0 mmol) in tetrahydrofuran (0.5 ml), a solution of 3-(2'-bromopropionyl)-4,4-dimethyloxazolidin-2-one (150 mg; 0.6 mmol) and (1'R,3R,4R)-3-(1'-hydroxyethyl)-4-acetoxyazetidin-2-one (35 mg; 0.2 mmol) in tetrahydrofuran (1 ml) was added at 26° C., and the resultant mixture was stirred at the same temperature for 1 hour. A phosphate buffer (about 0.1 ml) was added thereto to decompose the reaction agent. The reaction mixture was extracted with ethyl acetate and the extract was dried over anhydrous magnesium sulfate. The solvent was distilled off under reduced pressure to give an oily residue, which was purified by thin layer chromatography (chloroform: acetone=1:1) to give a mixture of (1'R,1"R,3S,4R)-and (1'R,1"S,3S,4R)-3-(1'-hydroxyethyl)-4-[1"-(4''',4'''-dimethyloxazolidin-2'''-one-3'''-carbonyl)ethyl]-azetidin-2-one.

H-NMR δ(CDCl₃): 1.57 (3H, s), 1.58 (3H, s), 2.95 (0.18H*α, m), 2.98 (0.82H*β, m), 4.04 (1H, s), 4.05 (1H, s), 5.85 (0.18H*α, bs), 5.97 (0.82H*β, bs).

*α: signal of (1"S)-form; *β: signal of (1"R)-form.

overnight. The reaction mixture was diluted with water and extracted with dichloromethane. The extract was dried over anhydrous magnesium sulfate and the solvent was distilled off under reduced pressure. The residue was purified by thin layer chromatography (chloroform: ethyl acetate=4: 1) to give a mixture of (1'R,1"R,3S,4R)- and (1'R,1"S,3S,4R)-3-[1'-(t-butyldimethylsilyloxy)ethyl]-4-[1"-(4''',4'''-dimethyloxazolidin -2'''-one-3'''-carbonyl)ethyl]azetidin-2-one.

The formation ratio of (1'R,1"R,3S,4R)-form to (1'R,1"S,3S,4R)-form was determined to be 82:18 by NMR spectrum.

EXAMPLE 11

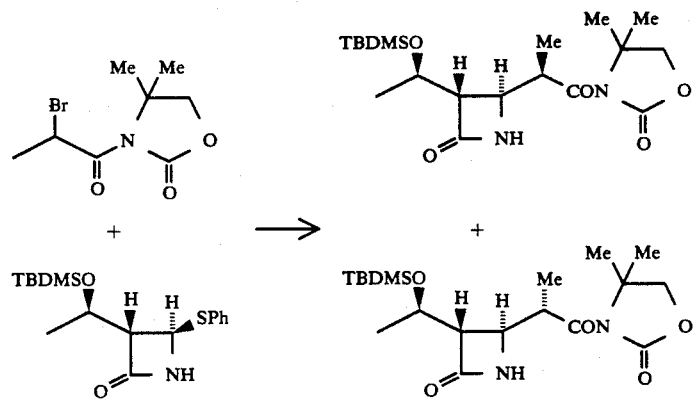

To a suspension of zinc powder (20 mg; 0.3 mmol) in tetrahydrofuran (0.5 ml), a solution of 3-(2'-bromopropionyl)-4,4-dimethyloxazolidin-2-one (50 mg; 0.2 mmol) and (1'R,3S,4R)-3-[1'-(t-butyldimethylsilyloxy)ethyl]-4-(phenylthio)azetidin-2-one (34 mg; 0.1 mmol) in tetrahydrofuran (1 ml) was added under reflux and followed by stirring for 2 hours. The reaction mixture was treated in the same manner as in Example 6-(2)-1 to give a mixture of (1'R,1"R,3S,4R)- and (1'R,1"S,3S,4R)-3-[1'-(t-butyldimethylsilyloxy)ethyl]-4-[1"-(4''',4'''-dimethyloxazolidin-2'''-one -3'''-carbonyl)ethyl]azetidin-2-one.

The formation ratio of (1'R,1"R,3S,4R)-form to (1'R,1"S,3S,4R)-form was determined to be 79:21 by NMR spectrum.

EXAMPLE 12

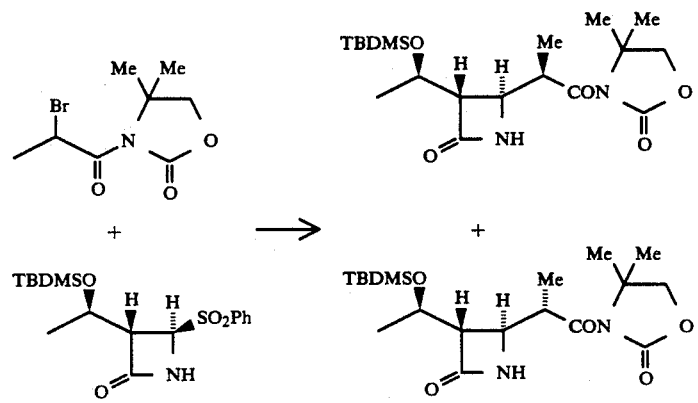

This product was dissolved in dimethylformamide (1 ml) and imidazole (82 mg; 1.2 mmol) and t-butyldimethylchlorosilane (133 mg; 0.88 mmol) were added thereto and followed by stirring at room temperature To a suspension of zinc powder (20 mg; 0.3 mmol) in tetrahydrofuran (0.5 ml), a solution of 3-(2'-bromopropionyl)-4,4-dimethyloxazolidin-2-one (50 mg; 0.2 mmol) and (1'R,3S,4R)-3-[1'-(t-butyldimethylsilyloxy)ethyl]-4-(phenylsulfonyl)azetidin-2-one (37 mg; 0.1 mmol) in tetrahydrofuran (1 ml) was added under reflux and followed by stirring for 2 hours. The reaction mixture was treated in the same manner as in Example 6-(2)-1 to give a mixture of (1'R,1"R,3S,4R)- and (1'R,1"S,3S,4R)-3-[1'-(t-butyldimethylsilyloxy)ethyl]-4-[1"-(4''',4'''-dimethyloxazolidin-2'''-one -3'''-carbonyl)ethyl]azetidin-2-one.

The formation ratio of (1'R,1"R,3S,4R)-form to (1'R,1"S,3S,4R)-form was determined to be 79:21 by NMR spectrum.

EXAMPLE 13-(1)

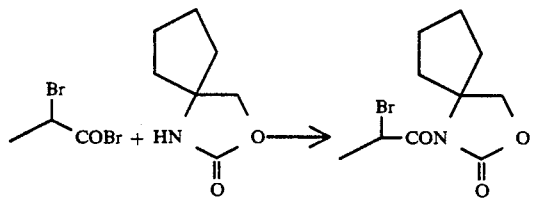

To a solution of 4,4-tetramethyleneoxazolidin-2-one (115 mg; 0.82 mmol) in dry tetrahydrofuran (0.8 ml), a 1.57 N solution of n-butyl lithium in hexane (0.57 ml; 0.90 mmol) was added at 0° C. and followed by stirring for 5 minutes. A solution of 2-bromopropionyl bromide (212 mg; 0.98 mmol) in dry tetrahydrofuran (0.2 ml) was added thereto at the same temperature. After stirring for 10 minutes, a phosphate buffer (pH 7.0) was added to the reaction mixture, which was extracted with ethyl acetate. The extract was washed with a 5% aqueous solution of sodium bicarbonate and then brine and dried over anhydrous magnesium sulfate. The solvent was distilled off, and the residue was purified by thin layer chromatography (benzene:ethyl acetate=10:1) to give 3-(2'-bromopropionyl)-4,4-tetramethyleneoxazolidin2-one.

IR (neat): 1770, 1695, 1435, 1295, 1273, 1105, 1080, 1050 cm$^{-1}$;

H-NMR δ (CDCl$_3$) 1.4-1.9 (4H, m), 1.82 (3H, d, J=6.6 Hz), 1.9-2.1 (2H, m), 2.2-2.5 (2H, m), 4.13 (2H, s), 5.78 (1H, q, J=6.6 Hz).

EXAMPLE 13-(2)

To a suspension of (1'R,3R,4R)-3-[1'-(t-butyldimethylsilyloxy)ethyl]-4-acetoxyazetidin-2-one (29 mg; 0.10 mmol) and zinc powder (20 mg; 0.30 mmol) in tetrahydrofuran (0.3 ml), a solution of 3-(2'-bromopropionyl)-4,4-tetramethyleneoxazolidin-2-one (55 mg; 0.20 mmol) in tetrahydrofuran (0.7 ml) was dropwise added under reflux and followed by stirring for 15 minutes. The reaction mixture was treated in the same manner as in Example 8-(2) to give a mixture of (1'R,1"R,3S,4R)- and (1'R,1"S,3S,4R)-3-[1'-(t-butyldimethylsilyloxy)ethyl]-4-[1"-(4''',4'''-tetramethyleneoxazolidin-2'''one-3'''-carbonyl)ethyl]azetidin-2-one.

The formation ratio of (1'R,1"R,3S,4R)-form to (1'R,1"S,3S,4R)-form was determined to be 85:15 by NMR spectrum.

IR (CHCl$_3$) 3420, 1760, 1690, 1373, 1278, 1240, 1187, 1095 cm$^{-1}$;

H-NMR δ (CDCl$_3$): 0.06 (3H, s), 0.07 (3H, s), 0.87 (0.85×9H*$^\beta$, s), 0.88 (0.15×9H*$^\alpha$, s), 1.0-2.5 (14H, m), 2.82 (0.15H*$^\alpha$, dd, J=1.5 and 5.1 Hz), 3.04 (0.85H*$^\beta$, m), 5.86 (0.15H*$^\alpha$, broad s), 5.93 (0.85H*$^\beta$, broad s).

*α: signal of (1"S)-form; *β:signal of (1"R)-form.

REFERENCE EXAMPLE 13-(1)

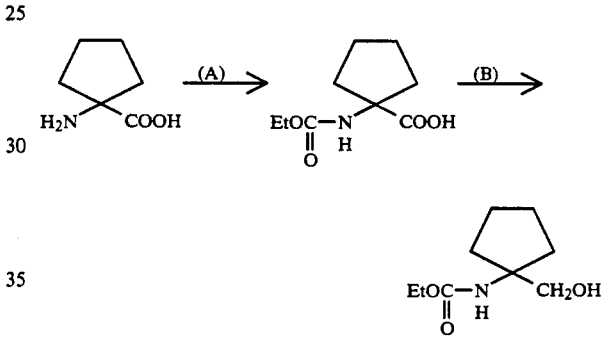

(A) To an aqueous solution (35 ml) of 1-amino-1-carboxycyclopentane (1.29 g; 10 mmol) and sodium bicarbonate (1.85 g; 22 mmol), a solution of ethyl chloroformate (1.30 g; 12 mmol) in diethyl ether (10 ml) was added at room temperature and followed by stirring for 6 hours. The organic layer was separated from the aqueous layer and extracted with a saturated aqueous solution of sodium bicarbonate. The combined aqueous layers were acidified with conc. hydrochloric acid and

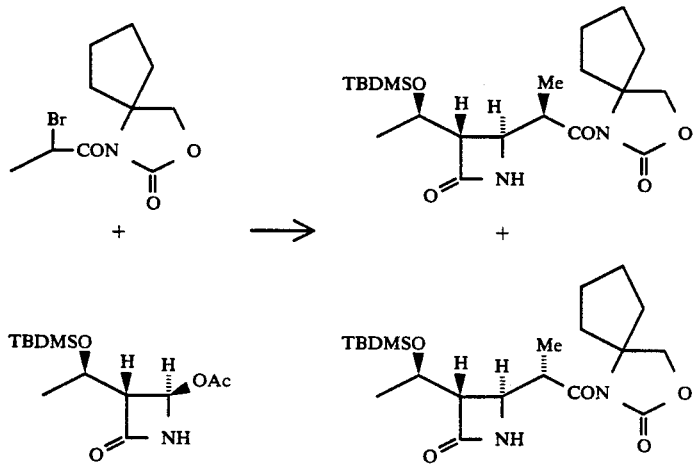

extracted with chloroform. The extract was dried over anhydrous magnesium sulfate and the solvent was removed under reduced pressure to give 1-ethoxycarbonylamino-1-carboxycyclopentane as a colorless solid.

IR (Nujol): 3340, 3070 (broad), 1715, 1658, 1520, 1270 cm$^{-1}$;

(B) To a solution of 1-ethoxycarboxylamine-1-carboxycyclopentane (0.80 g; 3.98 mmol) in tetrahydrofuran (10 ml), a solution of triethylamine (442 mg; 4.38 mmol) in tetrahydrofuran (1 ml) and then a solution of ethyl chloroformate (475 mg; 4.38 mmol) in tetrahydrofuran (1 ml) were dropwise added at −5° to −10° C. After removal of the resultant triethylamine hydrochloride by filtration, the filtrate was dropwise added to an aqueous solution (1.5 ml) of sodium borohydride (166 mg; 4.38 mmol) at −5° to 0° C. and followed by stirring for 1 hour. The reaction mixture was diluted with a 10% aqueous solution of sodium chloride and ethyl acetate. The organic layer was successively washed with a saturated aqueous solution of sodium bicarbonate and a 10% aqueous solution of sodium chloride and dried over anhydrous magnesium sulfate. After distilling off the solvent, the residue was purified by silica gel column chromatography (chloroform:ethyl acetate=1:0~9:1) to give 1-ethoxycarbonylamino-1-hydroxymethylcyclopentane.

IR (neat): 3375 (shoulder), 3325, 1710 (shoulder), 1680 cm$^{-1}$.

REFERENCE EXAMPLE 13-(2)

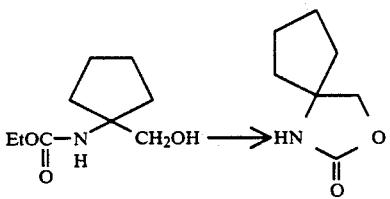

To a mixture of 1-ethoxycarbonylamino-1-hydroxymethylcyclopentane (0.25 g; 1.3 mmol) and diethyl carbonate (0.32 g; 2.7 mmol), potassium carbonate (3.7 mg; 0.027 mmol) was added, and the resultant mixture was stirred at 120° C. for 2 hours. After cooling to room temperature, the reaction mixture was diluted with brine and chloroform. The organic layer was washed with brine and dried over anhydrous magnesium sulfate. After distilling off the solvent, the residue was purified by thin layer chromatography (chloroform:ethyl acetate=1:1) to give 4,4-tetramethyleneoxazolidin-2-one as a colorless solid.

IR (Nujol): 3200 (broad), 1730 (broad), 1265, 1018 cm$^{-1}$;

H-NMR δ (CDCl$_3$): 1.5 - 2.0 (8H, m), 4.23 (2H, s), 5.74 (1H, broad s).

EXAMPLE 14-(1)

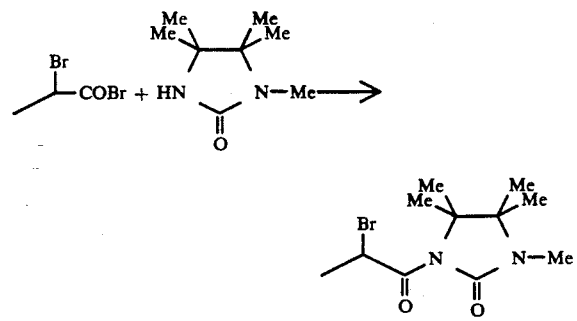

To a solution of 1,4,4,5,5-pentamethylimidazolidin-2-one (14 mg; 0.091 mmol) in dry tetrahydrofuran (0.2 ml), a 1.57 N solution of n-butyl lithium in hexane (0.06 ml; 0.1 mmol) was added at 0° C. After 5 minutes, a solution of 2-bromopropionyl bromide (24 mg; 0.11 mmol) in dry tetrahydrofuran (0.1 ml) was added thereto at the same temperature and followed by stirring for 10 minutes. A phosphate buffer (pH 7.0) was added to decompose the excess reaction agent. The aqueous layer was extracted with ethyl acetate, and the combined organic layers were successively washed with a 5% aqueous solution of sodium bicarbonate and brine and dried over anhydrous magnesium sulfate. After removal of the solvent under reduced pressure, the residue was purified by preparative thin layer chromatography (benzene:ethyl acetate=5:1) to give 3-(2'-bromopropionyl)-1,4,4,5,5-pentamethylimidazolidin-2-one.

IR (neat): 1715, 1680, 1415, 1358, 1280, 1240, 1130, 1105 cm$^{-1}$;

H-NMR δ (CDCl$_3$) 1.15 (6H, s), 1.36 (3H, s), 1.44 (3H, s), 1.79 (3H, d, J=6.8 Hz), 6.01 (1H, q, J=6.8 Hz).

EXAMPLE 14-(2)

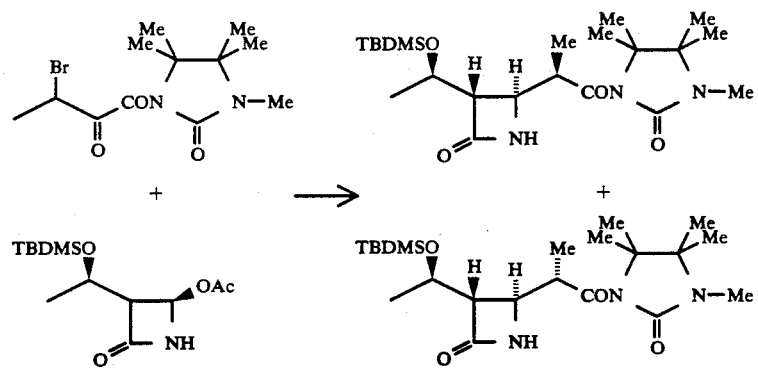

To a suspension of (1'R,3S,4R)-3-[1'-(t-butyldimethylsilyloxy)ethyl]-4-acetoxyazetidin-2-one (8.6 mg; 0.030 mmol) and zinc powder (5.9 mg; 0.090 mmol) in tetrahydrofuran (0.3 ml), a solution of 3-(2'-bromopropionyl) -1,4,4,5,5-pentamethylimidazolidin-2-one (17 mg; 0.059 mmol) in tetrahydrofuran (0.2 ml) was added in 15 minutes under reflux. After 1.5 hours, the reaction mixture was allowed to stand at room temperature, and ethyl acetate and a phosphate buffer (pH 7.0) were added thereto to decompose the excess reaction agent. The organic layer was successively washed with 1% hydrochloric acid, water, a 5% aqueous solution of sodium bicarbonate and brine and dried over anhydrous magnesium sulfate. The solvent was distilled off under reduced pressure to give a residue, which was purified by silica gel column chromatography (benzene:ethyl acetate=1:1) to give a mixture of (1'R,1''R,3S,4R) - and (1'R,1''S,3S,4R)-3-[1'-(t-butyldimethylsilyloxy)ethyl]-4-[1''-(1''',4''',4''',5''',5'''-pentamethylimidazolidin-2'''-one -3'''-carbonyl)ethyl]azetidin-2-one as a colorless solid.

The formation ratio of (1'R,1''R,3S,4R)-form to (1'R,1''S,3S,4R)-form was determined to be 84:16 by N-NMR spectrum.

IR (CHCl$_3$) 3420, 1750, 1705, 1667, 1420, 1370, 1280, 1135 cm$^{-1}$;

H-NMR δ (CDCl$_3$) 0.059 (3H, s), 0.062 (3H, s), 0.87 (0.84×9H*β, s), 0.88 (0.16×9H*α, s), 1.11 (3H, s), 1.12 (3H, s), 1.37 (3H, s), 1.39 (3H, s), 2.77 (3H, s), 3.03 (0.84H*β, m), 5.82 (0.16H*α, bs), 5.94 (0.84H*β, broad s).

*α: signal of (1''S)-form; *β:signal of (1''R)-form.

REFERENCE EXAMPLE 14-(1)

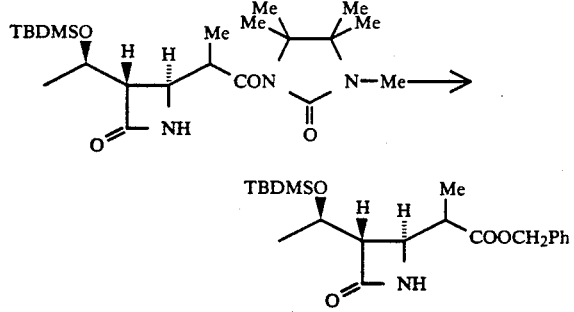

A mixture of (1'R,1''R,3S,4R) and (1'R,1''S,3S,4R) -3-[1'-(t-butyldimethylsilyloxy)ethyl]-4-[1''',4''',4''',5''',5'''-pentamethylimidazolidin-2'''-one-3'''-carbonyl)ethyl]azetidin-2-one prepared in Example 14-(2) (mixing ratio, 84:16) (4.7 mg; 0.011 mmol) was dissolved in tetrahydrofuran (0.1 ml), to which a 0.52 M solution of lithium benzyl alkoxide in tetrahydrofuran (0.1 ml) was added at 0° C. After stirring the mixture at room temperature for 3 days, the solvent was distilled off under reduced pressure to give an oily residue, which was purified by thin layer chromatography (n-hexane:diethyl ether=1:2) to give a mixture of (1'R,1''R,3S,4R)- and (1'R,1''S,3S,4R)-3-[1'-(t-butyldimethylsilyloxy)ethyl]-4-1'''-(benzyloxycarbonyl)ethyl]azetidin-2-one as a colorless solid.

The formation ratio of (1'R,1''R,3S,4R)-form to (1'R,1''S,3S,4R)-form was determined to be 76:24 by H-NMR spectrum.

REFERENCE EXAMPLE 14-(2)

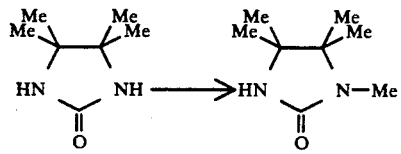

To a solution of 4,4,5,5-tetramethylimidazolidin-2-one (100 mg; 0.70 mmol) in dry tetrahydrofuran (5 ml), a 1.57 N solution of n-butyl lithium in hexane (0.49 ml; 0.77 mmol) was added at 0° C. After stirring at the same temperature for 5 minutes, a solution of methyl iodide (109 mg; 0.77 mmol) in tetrahydrofuran (1 ml) was added at 0° C., followed by stirring at room temperature for 10 minutes. To the reaction mixture, a saturated aqueous solution of potassium dihydrogen phosphate was added to decompose the excess reaction agent, and the resulting mixture was extracted with ethyl acetate. The extract was washed with brine and dried over anhydrous magnesium sulfate. The solvent was distilled off under reduced pressure to give an oily residue, which was purified by thin layer chromatography (chloroform:acetone=1:1) to give 1,4,4,5,5-pentamethylimidazolidin-2-one as a colorless solid.

IR (Nujol): 3200 (broad), 1695, 1235, 1160, 1150, 1125 cm$^{-1}$;

H-NMR δ (CDCl$_3$) 1.11 (6H, s), 1.17 (6H, s), 2.68 (3H, s), 4.47 (1H, bs).

What is claimed is:

1. A process for preparing a compound of the formula:

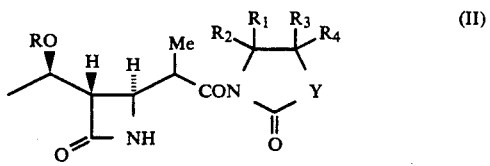

wherein R is a hydrogen atom or a protective group for hydroxyl, $R_1$ and $R_2$ are each a $C_1$-$C_8$ alkyl group or a combined together to form a $C_2$-$C_8$ alkylene group, $R_3$ and $R_4$ are each a hydrogen atom or a $C_1$-$C_8$ alkyl group or combined together to form a $C_2$-$C_8$ alkylene group and Y is an oxygen atom or a nitrogen atom substituted with $C_1$-$C_8$ alkyl or aryl in an R-isomer rich state, which comprises reacting a compound of the formula:

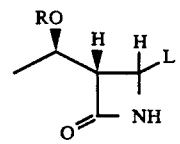

wherein L is a leaving group selected from the group consisting of $C_1$-$C_3$ alkylcarbonyloxy, arylcarbonyloxy, arylthio and arylsulfonyl, and R is as defined above, with a compound of the formula:

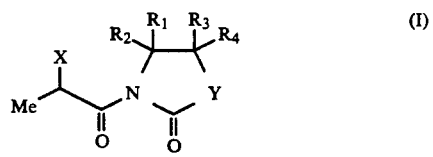

wherein X is a halogen atom and $R_1$, $R_2$, $R_3$, $R_4$ and Y are each as defined above in an ethereal solvent selected from the group consisting of ethers, hydrocarbons and aprotic solvents in the presence of zinc powder at a temperature of 0° to 100° C., and recovering as product a compound of said formula (II).

2. The process according to claim 1, wherein $R_1$ and $R_2$ are the same and each a $C_1$-$C_8$ alkyl group or combined together to form a $C_2$-$C_8$ alkylene group, $R_3$ and $R_4$ are the same and each a hydrogen atom or a $C_1$–$C_8$ alkyl group or combined together to form a $C_2$–$C_8$ alkylene group and Y is an oxygen atom or a nitrogen atom substituted with $C_1$–$C_8$ alkyl.

3. The process according to claim 1, wherein $R_1$ and $R_2$ are each a methyl group, $R_3$ and $R_4$ are each a hydrogen atom and Y is an oxygen atom.

4. The process according to claim 1, wherein the ethereal solvent is selected from the group consisting of diethyl ether, dibutyl ether, tetrahydrofuran, dioxane and 1,2-dimethoxyethane.

5. The process according to claim 4, wherein the ethereal solvent is selected from the group consisting of tetrahydrofuran, dioxane and 1,2-dimethoxyethane.

6. The process according to claim 1, wherein the reaction is effected at a temperature of 60° to 100° C.

7. The process according to claim 1, wherein the product is obtained in an R-isomer:S-isomer ratio of not less than 3.

8. A process for preparing a compound of the formula:

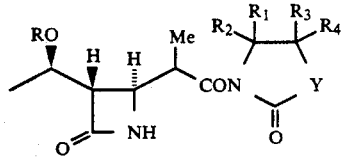
(II)

wherein R is a hydrogen atom or a protective group for hydroxyl, $R_1$ and $R_2$ are each a $C_1$–$C_4$ alkyl group or combined together to form a $C_4$–$C_5$ alkylene group, $R_3$ and $R_4$ are each a hydrogen atom or a $C_1$–$C_4$ alkyl group or combined together to form a $C_4$–$C_5$ alkylene group and Y is an oxygen atom or a nitrogen atom substituted with $C_1$–$C_4$ alkyl or aryl in an R-isomer:S-isomer ratio of not less than 3, which comprises reacting a compound of the formula:

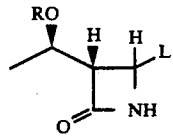

wherein L is a leaving group selected from the group consisting of acetoxy, benzyloxy, phenylthio and phenylsulfonyl, and R is as defined above with a compound of the formula:

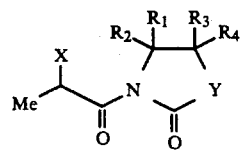
(I)

wherein X is a halogen atom and $R_1$, $R_2$, $R_3$, $R_4$, and Y are each as defined above in an ethereal solvent selected from the group consisting of tetrahydrofuran, dioxane and 1,2-dimethoxyethane in the presence of zinc powder at a temperature of 60° to 100° C., and recovering as product a compound of said formula (II).

* * * * *